United States Patent [19]

Sitrick

[11] Patent Number: 4,492,235
[45] Date of Patent: Jan. 8, 1985

[54] SYSTEM AND METHOD FOR PREDICTING VENTRICULAR TACHYCARDIA BY DERIVATIVE ANALYSIS

[75] Inventor: David H. Sitrick, Highland Park, Ill.

[73] Assignee: Arrhythmia Research Technology, Inc., Freeport, Tex.

[21] Appl. No.: 347,988

[22] Filed: Feb. 11, 1982

[51] Int. Cl.³ .............................................. A61B 5/04
[52] U.S. Cl. .................................................... 128/705
[58] Field of Search .............................. 128/695–696, 128/702–705, 708; 364/415, 417

[56] References Cited

U.S. PATENT DOCUMENTS

| | | | |
|---|---|---|---|
| 3,087,487 | 4/1963 | Clynes | 128/731 |
| 3,171,892 | 3/1965 | Tanple | 128/731 |
| 3,552,386 | 1/1971 | Horth | 128/703 |
| 3,823,708 | 7/1974 | Longhorn | 128/702 |
| 3,927,377 | 12/1975 | Nothing | 128/708 |
| 3,978,856 | 9/1976 | McPhee | 128/705 |
| 4,023,564 | 5/1977 | Valiquette et al. | 128/708 |
| 4,261,309 | 4/1981 | Allor | 128/696 |
| 4,296,755 | 10/1981 | Judell | 128/705 |
| 4,325,384 | 4/1982 | Blaser | 128/708 |

FOREIGN PATENT DOCUMENTS 0052512  5/1982  European Pat. Off. ............. 128/702

OTHER PUBLICATIONS

Fraden et al., "Medical & Biological Engineering & Computing", vol. 18, No. 2, Mar. 1980, pp. 125–132.
Principe et al., "Proceedings of Southwestern 1978 Region 3 Conference, Atlanta GA", Apr. 10–12, 1978, pp. 24–27.
Taylor et al., "Medical & Biological Engineering", vol. 12, No. 4, Jul. 1974, pp. 493–502.
Rabiner et al., "IEEE Transactions on Audio & Electroacoustics", vol. 19, No. 3, Sept., 1971, pp. 200–207.

Primary Examiner—William E. Kamm
Attorney, Agent, or Firm—Fitch, Even, Tabin & Flannery

[57] ABSTRACT

A system for predicting ventricular tachycardia from electrocardiograph input waveforms. A high pass filter provides an output responsive to the input waveforms. A time derivative of the filter output is generated to produce waveforms which can be compared to a standard. In one embodiment, the input waveforms are digitized prior to processing by the filter means. In another embodiment, digitized input waveforms are signal averaged prior to processing by the filter. The filter can be a finite impulse response filter of an infinite impulse response filter. In an alternate embodiment, a ventricular tachycardia prediction system for use with ECG waveforms having cyclical characteristics is disclosed. The ECG waveforms are periodically sampled during each of a plurality ECG cycles. A filter unidirectionally filters the signals for each ECG cycle so as to provide a filter output systematically related to the high frequency content of the input. A reference signal is provided for ventricular tachycardia prediction. The filter output is compared to the reference signal, and a propensity for episodes of ventricular tachycardia is indicated responsive to the comparison.

26 Claims, 27 Drawing Figures

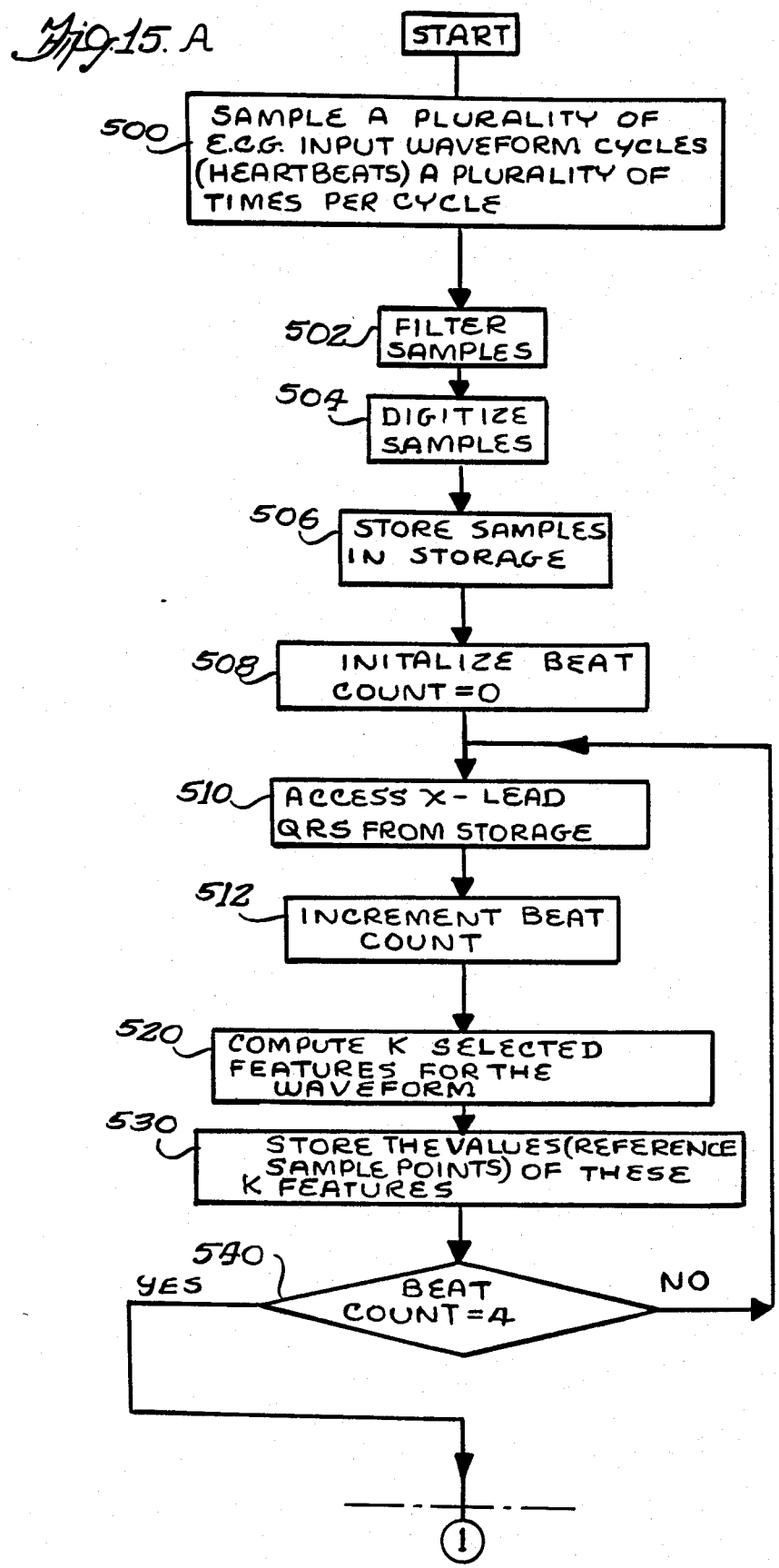
Fig. 15. A

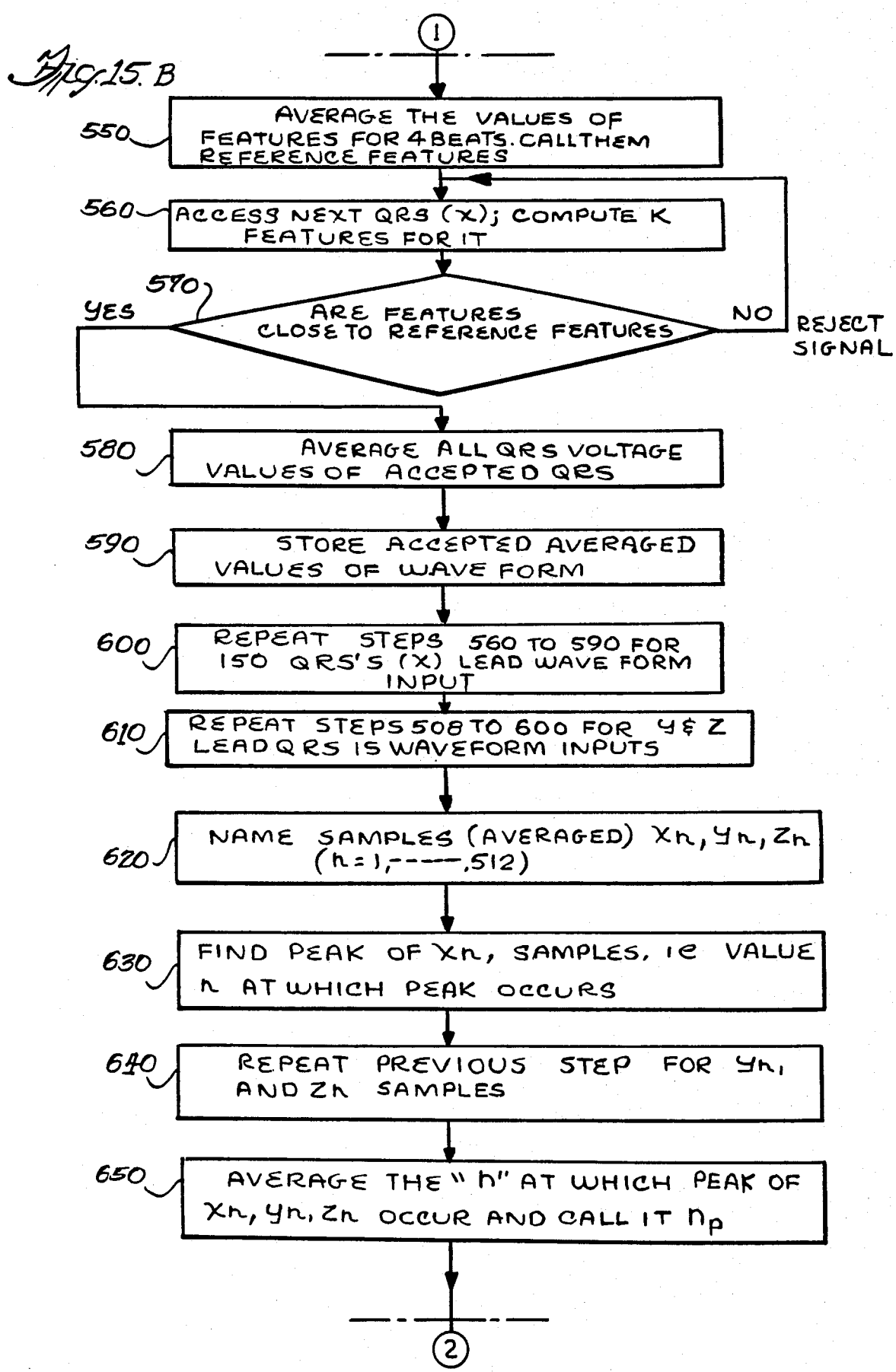

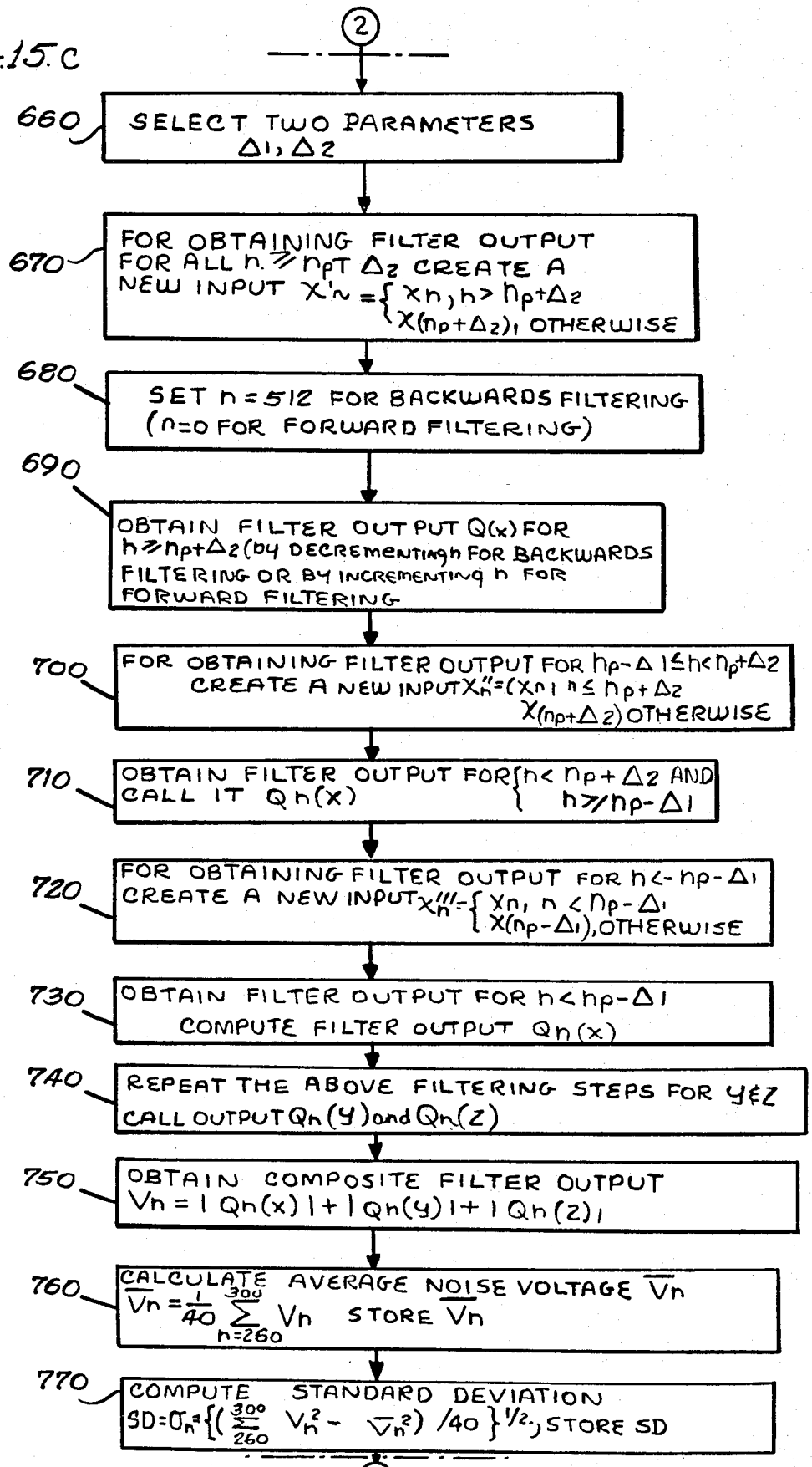
Fig. 15.C

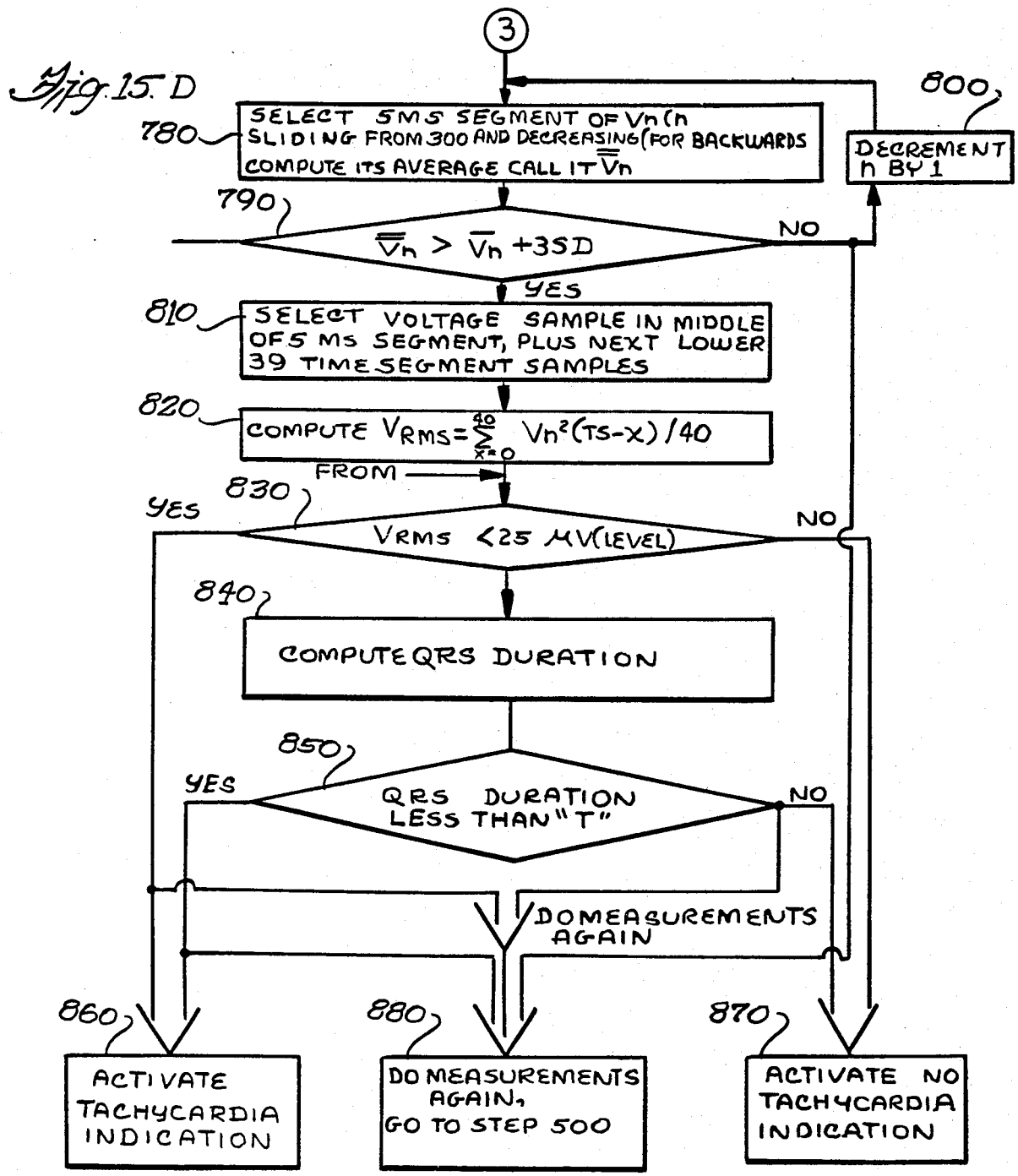
Fig. 15.D

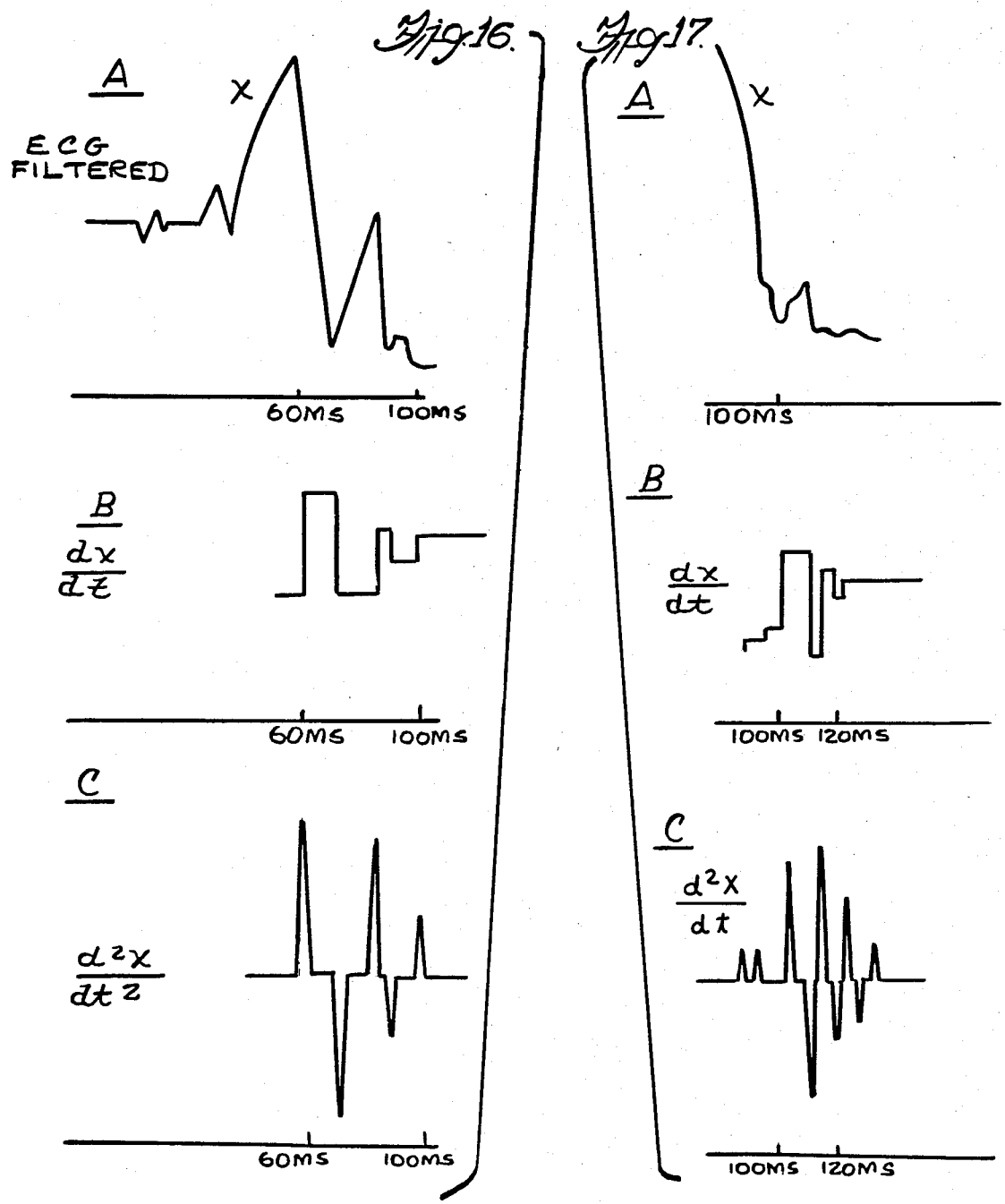

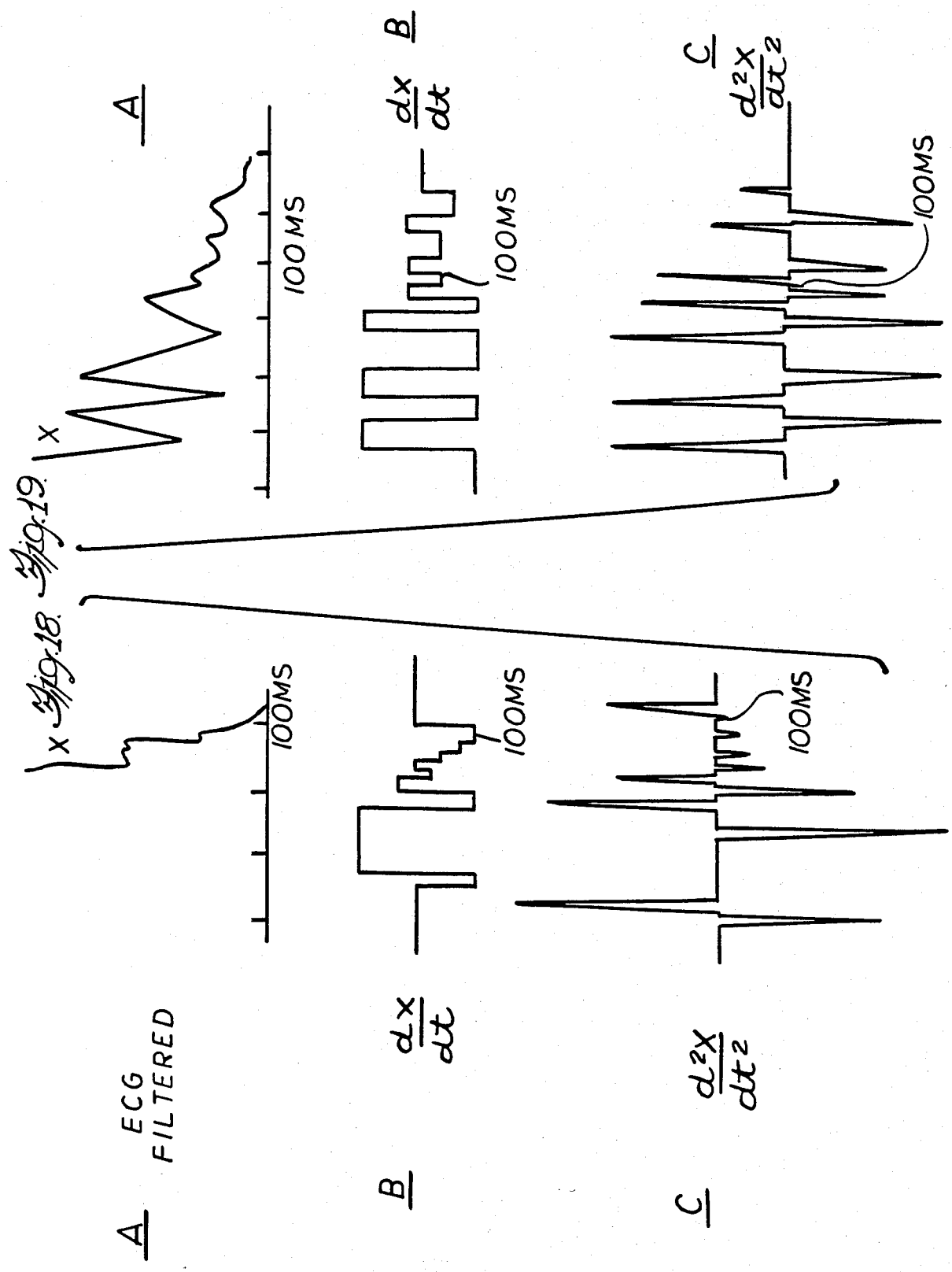

SYSTEM AND METHOD FOR PREDICTING VENTRICULAR TACHYCARDIA BY DERIVATIVE ANALYSIS

This invention relates to electrocardiography and more particularly to an improved system and method for predicting potential ventricular tachycardia in a patient.

Sudden death from accute arrhythmia is a major risk in the first few hours after a myocardial infarction. During the first days, the incidence of ventricular arrhythmia is approximately 90%. The percentage of arrhythmias decreases considerably after the first several days but still presents a substantial risk to the myocardial infarct patient. Statistically, without treatment, approximately 50% of all infarct patients will eventually die of ventricular arrhythmia.

A reproducible and consistent ability to predict a patient's propensity for lapsing into an arrhythmia is needed. Several investigators employing signal averaging techniques have detected, on the body surface small amplitude high frequency potentials in the late QRS and ST-segments of electrocardiograms in patients and animals prone to ventricular tachycardia. (Uther, et al.: "The Detection of Delayed Activation Signals of Low Amplitude in the Vector Cardiogram of Patients with Recurrent Ventricular Tachycardia by Signal Averaging", in *Management of Ventricular Tachycardia—Role of Mexiletine*, edited by E. Sandoe, et al., Excerpta Medica, Amsterdam, 1978, pp. 80-82). Uther, et al. found that these potentials did not occur in healthy, young people and suggested that they represented areas of delayed myocardial depolarization.

Obviously, if it can be shown that the high frequency signal in the late QRS of a myocardial infarct patient is common to most, if not all, infarct patients who are subject to ventricular tachycardia, an important new diagnostic tool would be available. Technically, however, it is extremely difficult to isolate, accurately, high frequency signals late in the QRS complex. A filter must be used to eliminate the lower frequency portions and to analyze the late QRS for high frequency content. Unfortunately, substantially all filters employed in the prior art "ring" for a period of time after application of the relatively high energy, initial portion of the QRS waveform. This ringing effectively hides any low amplitude, high frequency portions in the QRS.

Some prior art systems dealt with ringing problems by plotting or displaying the waveforms at various resolutions and left prediction to the doctor. Another approach which has been utilized in the prior art is to reverse time filter the waveform to analyze the tail of the QRS, and then to forward time filter the waveform to determine the start of the QRS portion and therefrom to deduce the QRS width. The filters employed in prior systems have predominantly been recursive, sharp cut-off filters.

In a large clinical trial supervised by Dr. Michael Simson, University of Pennsylvania, using an electrocardiographic analysis system as described in pending U.S. patent application Ser. No. 208,219, now U.S. Pat. No. 4,422,459 it was found that 92% of postmyocardial infarct patients who were subject to ventricular tachycardia, did, indeed, exhibit a distinctive high frequency signal tail in their late QRS signal. This signal was present in only 7% of post infarct patients who were free of ventricular tachycardias. In addition, it was found that a patient subject to ventricular tachycardia will exhibit a QRS signal of substantially longer duration than patients without ventricular tachycardia.

SUMMARY OF THE INVENTION

It is an object of the present invention to predict potential ventricular tachycardia with unidirectional time filtering while overcoming filter ringing problems.

In accordance with the illustrated embodiments of the present invention, X, Y, and Z electrocardiographic signals from a patient are converted from analog to digital values, and stored, then processed to select only normal or typical QRS waveforms. The selected waveforms are signal averaged over several hundred beats to obtain a relatively noise-free composite QRS. The latter portions of the X, Y, and Z digital QRS signals are then applied to an adaptive high pass filter. The resulting filtered outputs are combined to create a composite filtered QRS waveform. The last 40 (or so) milliseconds of the filtered composite is isolated and measured to obtain an indication of the level of high frequency energy content indicative of a propensity for episodes of ventricular tachycardia. The overall QRS waveform is also processed in the same time order to determine its total duration which provides a second indication of a propensity for Ventricular Tachycardia.

Alternatively, the first or higher order derivatives of the filtered and unfiltered outputs are compared with a standard to determine ventricular tachycardia. The patient who has a propensity for ventricular tachycardia will have a filtered waveform which, when a derivative is taken, will exhibit a much different pattern than a healthy patient. By comparing the two patterns, an indication can be generated which will be useful in predicting which patients may exhibit tachycardia. The number of transitions, time position of the transitions, and area displaced by the pulse widths are all criteria used in determining whether the pattern of a patient under examination is abnormal.

Further features and advantages of the invention will become more readily apparent from the following detailed description, when taken in conjunction with the accompanying drawings, wherein:

FIGS. 15A-15D are a simplified flowchart of the overall processing flow utilized to predict potential Ventricular Tachycardia from an ECG input according to an embodiment of the present invention;

FIGS. 16-21 are waveform diagrams of the outputs of various high pass filters before and after a derivative has been taken for patients with and without ventricular tachycardia.

DESCRIPTION OF THE ILLUSTRATED EMBODIMENTS

Figure 1:
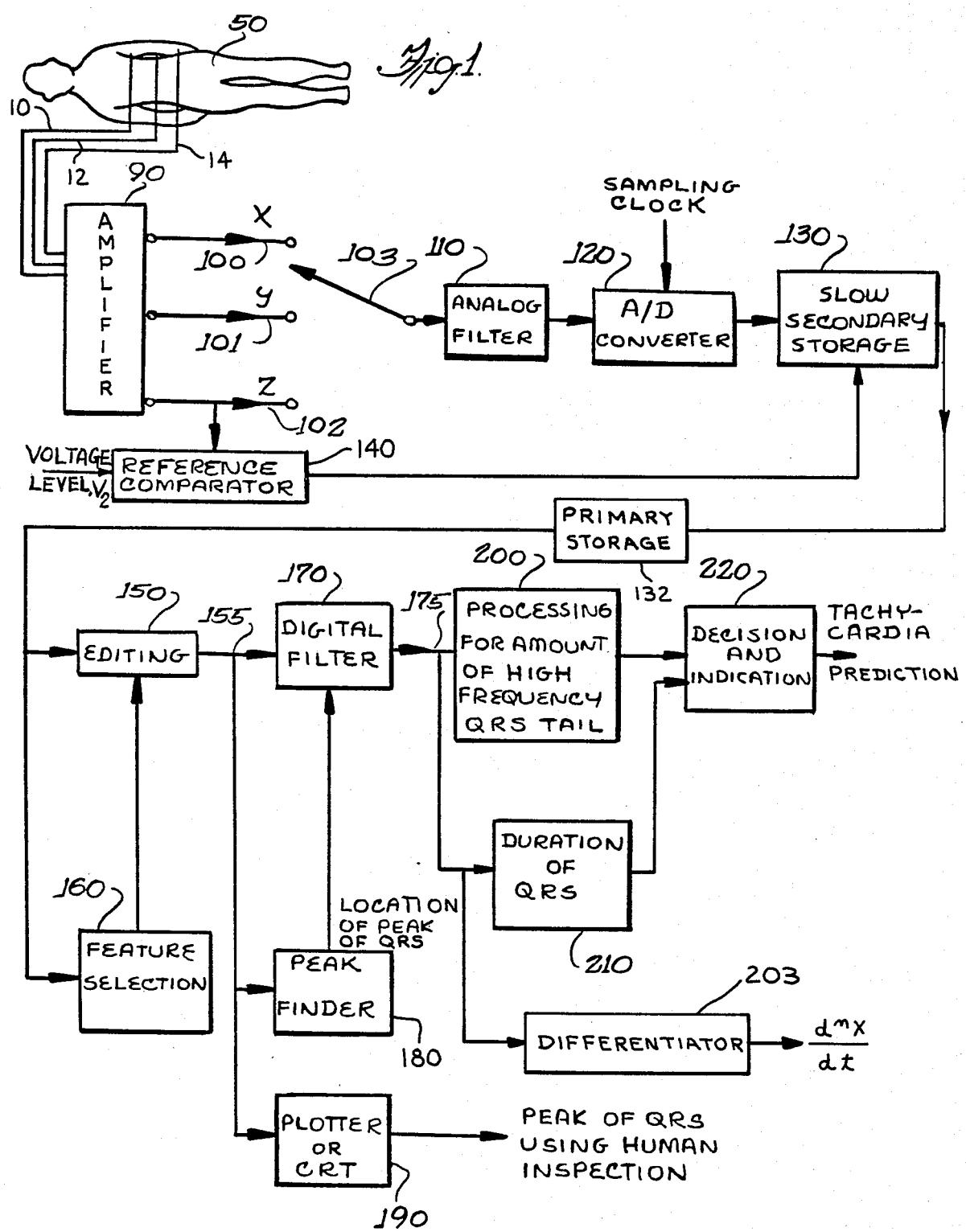
FIG. 1 is a block diagram of an electronics based embodiment of the invention.

Referring now to FIG. 1, a block diagram of an apparatus constructed in accordance with the present invention is shown. Each of leads 10, 12 and 14 is a bipolar electrocardiographic electrode lead. The X electrodes are applied to the patient's midaxillary line at the fourth intercostal space (under the left arm between the fourth and fifth ribs). The Y electrodes are placed at the superior aspect of the sternum and the proximal left leg. The Z electrode is at the "$V_2$" position (left of sternum at the nipple line), and the other electrode is directly posterior. Each of the respective X, Y, and Z leads (10, 12 and 14) is coupled to a respective one of three ECG amplifiers 90 (such as Analog Devices Model 283J isolation amplifier). The output of each amplifier is passed from switch contact 100, 101, and 102, through switch 103, and to a low pass filter 110. Filter 110 characteristically attenuates all signals above 250 Hz. The output from filter 110 is fed to an analog to digital converter 120 which samples the incoming voltage every millisecond and converts it to a 12-bit binary signal (such as an Analog Device Ad572 used at a sample rate of 1,000 samples per second). The time segment outputs from A to D converter 120 are stored in the order sampled in storage means 130, such as on tape, disk, semiconductor memory or other electronic or magnetic storage means.

The X, Y, and Z ECG signals on contacts 100, 101, 102 are sequentially connected to the filter 110 and to A to D converter 120 by the operation of the switch 103. The filter 110 can be replaced by any of a number of preprocessing functions. The outputs from all contacts are sampled for 133 seconds at the 1000 sample/sec rate to obtain the necessary continuum of recorded signals.

The switch 103 can alternatively be a multiplexer for simultaneously measuring the X, Y and Z leads signals during each ECG cycle. Furthermore, the switch 103 can be eliminated and three separate processing paths each having an analog filter and an A/D converter can be coupled with each of the X, Y and Z amplifier outputs to a respective analog filter, A/D converter, and storage means.

In either of these alternatives, only a single 133 second period is required to record a continuum of X, Y and Z leads signals.

Sometimes the leads of the ECG are multiphasic, noisy, or contain extra beats. It is therefore desirable to select the ECG lead for a reference which has the best unambiguous trigger and least abnormal output. While any of the X, Y or Z leads can be chosen, experimentation has shown the Z lead to usually be the best.

Therefore, the output from the Z ECG amplifier on contact 102 is also coupled to an input of reference comparator 140. A bandpass filter (such as 8-40 Hz) can be inserted between the ECG lead output signal from the amplifier and the reference comparator 140 to provide a noise free signal. A reference voltage $V_2$ is coupled to a second input of the reference comparator 140, which sets the comparison level. When the QRS portion of the Z lead appears on line 102 and passes through the reference voltage, the reference comparator generates a reference bit which is recorded along with the corresponding time segment output of A to D converter 120. This reference bit enables all QRS waves to be overlaid, one on another, for selection and averaging purposes. Alternatively, the reference comparator can use parameters in addition to or instead of voltage level. For example, the maximum or minimum slope can be used to establish the reference bit position. The reference time is a common time from lead to lead (X, Y, Z) and from ECG cycle to cycle.

The samples of the waveform are taken from the secondary storage 130 and put into a fast primary storage 132 from which an editing function 150 is performed. The editing function works in conjunction with a feature selection function 160 to discard waveforms which are nonstandard. Alternatively, where a large primary storage is available, no secondary storage need be employed. Particular features of the waveform are preselected as standard, such as by experimentation, and any waveform not meeting the standard is rejected by the feature selection means 160. All waveforms meeting the standard are then averaged to reduce noise in the editing function 150. The edited, averaged waveforms for the X, Y, and Z leads are then passed on via coupling node 155 to an adaptive digital high pass filter 170, preferably of the finite impulse response type, and to a peak finder 180 which locates the peak of the QRS complex of the ECG input. The digital filter response is a function of the location of this peak in the illustrated embodiments, and does not require both forward and reverse filtering; either forward only or reverse only filtering is sufficient.

The filtered output is passed to the two subsystems 200 and 210. One subsystem, 200, provides means for determining the amount of high frequency energy in the tail of the QRS portion of the ECG input. The segment of the averaged waveforms forming the tail of the QRS section is first accurately determined, as will be described later, and then the energy in that tail is measured. Additionally the filtered output 175 is analyzed by means 210 which determines the duration of the QRS complex from the signal at node 175. The QRS duration and high frequency tail content are correlated by decision means 220 with emperically derived standards for content and duration to predict Ventricular Tachycardia. The prediction of ventricular tachycardia can be made by the decision and indication means 220 based on either or both the duration of the QRS complex and the high frequency energy at the tail of the QRS complex. If both these indicators are positive, indicating probable Ventricular Tachycardia, then the prediction is positive. If both are negative, then the diagnosis is negative. If one of these indicators is positive and the other is not, then the decision subsystem 220 can provide an indication of the conflicting data and new data can be taken for confirmation. A plotter or CRT 190 can also be used so that a physician can look at the edited/averaged waveform being processed and make an independent judgment. If the peak finder subsystem 180 is not implemented in a particular embodiment, then human inspection of the edited/averaged waveform can be used to determine the peak of the QRS complex of the ECG input. It is not necessary to know the precise location of the peak in order to practice the present invention, and an approximate peak location is adequate.

Figure 2:
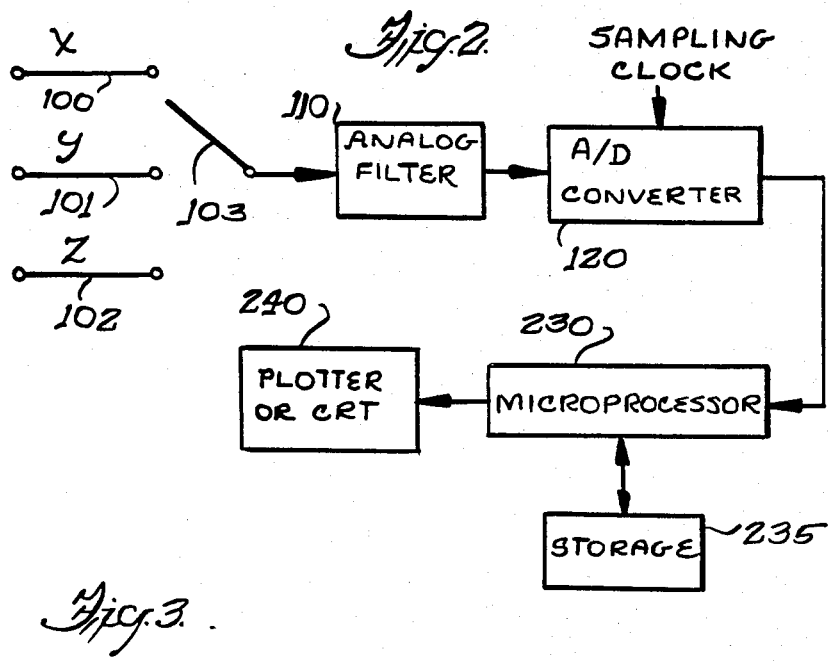
FIG. 2 is a block diagram of a microprocessor based embodiment of the invention.

Referring to FIG. 2, an alternate embodiment of the system of FIG. 1 is shown. The subsystem functions of editing, 150, feature selection, 160, digital filtering, 170, peak finding, 180, processing for the amount of high frequency energy in the QRS tail, 200, duration of the QRS complex, 210, and the decision and indication means, 220, of FIG. 1 are implemented in a computer system utilizing a software program. The computer system may be comprised of a microprocessor based system, minicomputer, or other computer. There are several reasonably inexpensive microprocessors which will perform the necessary functions at adequate speeds.

A general description of the operation of the systems of FIGS. 1 and 2 shall now be described. First, the Z lead waveform of the ECG input is analyzed to establish a reference waveform. (Alternatively, either the X or Y waveform of the ECG input may be first analyzed to determine the reference.) It is analog filtered, sampled, digitized and stored (where digital filtering is used), compared to the reference voltage (which has been previously predetermined), and a reference bit is generated at the time segment corresponding to the Z waveform value equal to the reference voltage. Each new waveform that is sampled is then processed using the reference bit as thus described. Where 512 samples are utilized for each ECG cycle, each sample is stored in a slow secondary storage means 130 (or where available in a portion of a large primary storage) for each of the X, Y, and Z waveforms of the ECG input, for later use by the system. The reference bit technique is one of several which may be used to eliminate erroneous waveforms from being utilized in analysis by the system.

Figure 3:
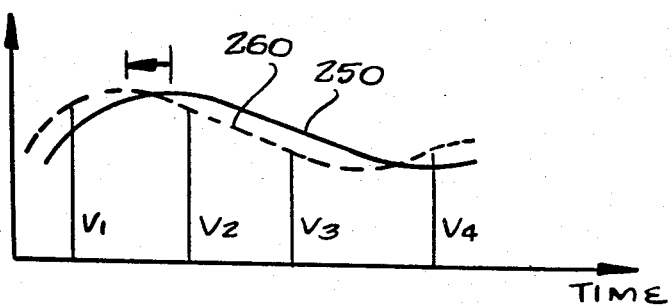
FIG. 3 is a graphical representation of a waveform registration technique in accordance with one embodiment of the present invention.

Referring to FIG. 3, a graph illustrating one waveform registration technique is shown. Many techniques are available for proper registration of the waveforms to one another from cycle to cycle. The following alternatives are given as examples.

(1) The incoming waveform is compared with one voltage such as the peak voltage value $V_P$ and the time instant at which the incoming waveform equals the peak voltage is recorded. The other incoming waveforms are shifted such that each is properly registered with respect to this one point.

(2) The incoming waveform is compared with several reference voltages and the time instance at which these voltages occurred on the incoming waveform are recorded, as illustrated in FIG. 3. Each incoming waveform is then shifted right or left until the match to these reference voltages is the best. As illustrated in FIG. 3, the solid line 250 is the new waveform and V1, V2, V3, and V4 are reference voltages from the reference waveform 260 (dotted) which have been previously determined. By shifting the solid waveform to the left in the illustrated example, better match and proper registration is obtained for the illustrated example of FIG. 3.

The feature selection function 160 and editing function 150, of FIG. 1, may be performed in hardware or software and many techniques can be used. For example, template selection or signal averaging can be used. Subsequent waveforms can be selected by adjusting DC levels and time shifts in both plus and minus directions relative to the template. Initially, a single beat, including a QRS, is accessed from the secondary storage and placed in a buffer register. The reference bit is here employed to grossly acquire the reference location points on the QRS. Starting with the reference bit and ending with a reference location 128 milliseconds thereafter, eight location samples are selected and stored. This process continues for four QRS counts, and enables the establishment of the initial template against which succeeding QRS signals will be tested. After the fourth QRS signal is stored, the maximum and minimum voltage values for each of the eight voltage points on the four recorded QRS waveforms are tabulated and become the initial template. Statistical analysis can be used to reject noisy signals from use in the template. Then, the next QRS signal is selected, its eight voltage points are determined and stored, and each point is selectively tested against the stored maxima and minima to determine whether it falls within or without the respective values. If it is found that there is a mismatch in any one of the eight points, the signal is rejected as not being a QRS or being some other artifact which is not of interest. If all eight points fall within the maxima and minima, the waveform is accepted as a QRS, and its 512 voltage points, spanning the accepted QRS, are then averaged with the corresponding 512 points of the previously stored QRS signals, and the resulting averaged value stored in a buffer memory. This routine is repeated for 150 QRS's which are subsequently passed through the template, averaged, and then stored to accomplish a composite-averaged QRS wave for the X lead. The template voltage minimum and maximum test points can be updated during the processing to assure accurate QRS selection. The same procedure is then repeated for the Y and Z leads, and the averaged values for each of the composite Y and Z QRS signals also are respectively stored in the buffer memory. The buffer memory can form a part of the editing means 150, or can be provided as a separate means, and can utilize semiconductor, bubble, disk and/or other storage.

The above processing greatly reduces the noise inherent in the QRS signal—by the square root of the number of averaged beats—and provides three averaged QRS waveforms which are relatively noisefree and suitable for subsequent processing. Approximately 150 beats per lead are signal-averaged and recorded. At this point, the recorded QRS waveforms can be coupled to the remaining processing means and/or can be plotted out on plotter 190 (or 240) for examination by the physician. The plot also enables the physician to pick out the midpoint of the QRS for the subsequent filtering step, as a substitute or verification for the peak finder means 180.

Other alternative techniques can also be employed. For example, in order to accept or reject a waveform for the averaging process, certain features of the reference waveform can be evaluated. These features can be called the reference features. If the new waveform has features which are not "significantly" different from the reference features then it is a "good" waveform and it is accepted for averaging; otherwise it is rejected. Some of the alternative reference features are:

(i) Value of the voltages at certain prespecified times;

(ii) Values of the peak voltage and the time at which it occurs;

(iii) Reference times when the waveform is at, exceeds, or is below a certain voltage level.

(iv) Sum of the samples of the X, Y, or Z lead inputs during each ECG cycle having an amplitude greater than a predefined threshold;

(v) Sum of the positive and negative values around a certain voltage level V. For example, if $V_n$ are samples, then $\Sigma(V_n-V)f(V_n-V)+\Sigma g(V_n-V)(V_n-V)$ where $f(V_n-V)=1$ if $(V_n-V)>0$, otherwise, $f(V_n-V)=0$; and $g(V_n-V)=1$ if $(V_n-V)\leq 0$ otherwise, $g(V_n-V)=0$.

(vi) A combination of features can also be used. These features can be referred to as $F_1, F_2, \ldots F_k$ (i.e. k separate features). The "k" reference features can be measured and denoted by values $F_{R1}, F_{R2}, \ldots F_{Rk}$. A new waveform is then accepted for averaging if its features $F_1, \ldots, F_k$ are not sufficiently different from the reference features, i.e.

Accept the waveform if $$\sum_{i=1}^{i=k} |F_{Ri} - F_i| \leq \text{threshold},$$

otherwise reject it.

The threshold is preselected, based on experiments. Different features can be given different importance by considering a weighted sum, i.e.

Accept the waveform if $$\sum_{i=1}^{i=k} W_i * |F_{Ri} - F_i| \leq \text{threshold}.$$

otherwise reject it, where weights $\{W_i\}$ are all positive. A feature that is considered most important, or which should be very close to the reference features, should have a high weight. The other features should have a smaller weight. All the accepted waveforms are averaged as described in the above section regarding signal averaging. Thus by averaging 150 waveforms, a composite averaged QRS waveform X-lead is created. Similarly composite-averaged Y and Z leads are created.

The next step is to find the peak of the QRS complex and its sample number, or the time at which this peak occurs. This is the function of the peak finder means 180 of FIG. 1. Several algorithms for determining the peak exist. One of these is described hereinafter, as follows:

Let samples occur at time $t_i$ having a corresponding value $V_i$.

Step 1: Assume the peak is at $t_1$ call it P.
Step 2: If $V_2 \leq V_1$, P is unchanged. If $V_2 > V_1$, then $P = t_2$. Step n: If $V_n \leq V_{n-1}$, P is unchanged. If $V_n > V_{n-1}$, $P = t_n$.

Thus by making sequential comparison, the peak of the QRS wave (from node 155) for each of the X, Y, and Z leads are found. This peak can be used in controlling the operation of the digital filter; as will be described hereafter in greater detail. As mentioned above, it is not necessary to precisely locate the peak, and therefore, the peak may be found by simple human observation of the averaged waveforms, either on a CRT or a plotter.

It is not required that both forward and backward filtering be utilized. Prior systems have used forward filtering to determine the beginning time point of the QRS complex, and used reverse time (backward) filtering in analyzing the QRS tail so that the high energy portion of the main QRS waveform does not spill over into the tail of the QRS (the high frequency energy content of which indicates a propensity for ventricular tachycardia). Bidirectional filtering was employed by prior systems because recursive, sharp cut off filters were used which exhibit significant ringing. The use of adaptive time varying, and/or Finite Impulse Response (FIR) filters can overcome this difficulty. Adaptive FIR filters also have much more flexibility and provide features which are difficult or impossible to obtain using the recursive filters.

Figure 4A:
FIGS. 4A-4C are graphical illustrations of the coefficients used in sampling for general finite impulse response (FIR) filters of the low pass type.
Figure 4B:
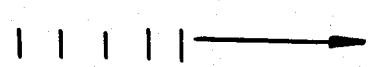
Figure 4C:
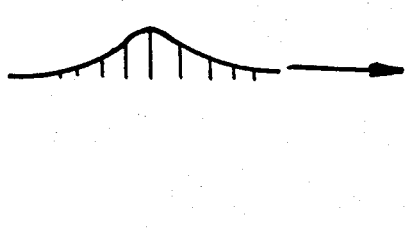

A simple high pass FIR filter can be modelled as having an input sequence $\{X_n\}$ and an output sequence $\{Y_n\}$, where $Y_n = X_n - \{\text{low pass filter output}\}$. The low pass filter can be modeled as $Y_n = 0.5X_n + 0.25(X_{n-1}+X_{n+1})$, as shown in FIG. 4a; $Y_n = 1/5(X_n + X_{n-1} + X_{n-2} + X_{n+1} + X_{n+2})$, for five (5) samples, as shown in FIG. 4b; or a low pass filter whose impulse response is an approximation to the Gaussian function, which would also have the Gaussian function as its frequency response, as shown in FIG. 4c. The stop response of the filter of FIG. 4c would be the Error Function, which is quite smooth with no ringing. (For greater detail on this see, for example, "Fourier Integral and its Applications", by Papoulis.)

Many other FIR configurations exist, which can be chosen to approximate a given frequency response characteristic. (For examples see "Digital Signal Processing" by Oppenheim and Schafer, Prentice Hall.)

Figure 5A:
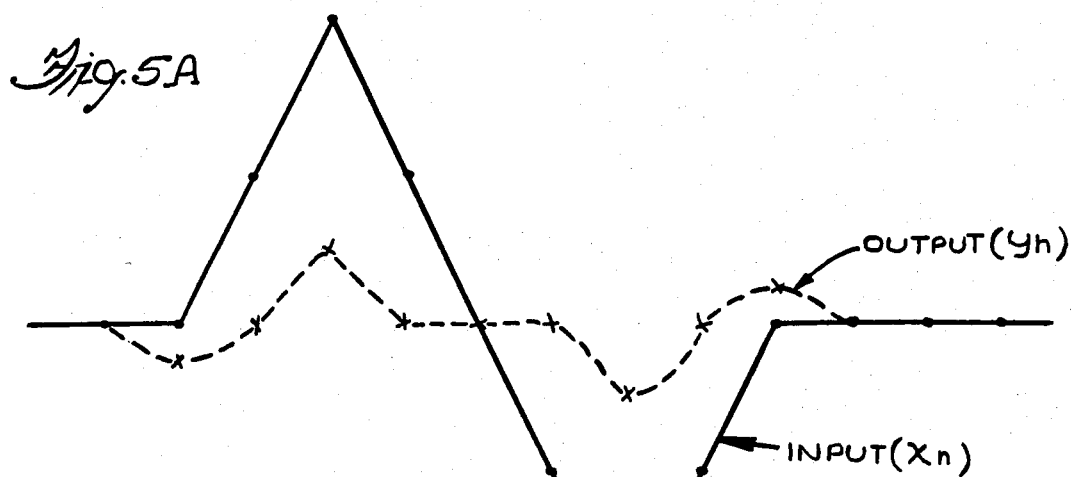
FIGS. 5A-5B are graphical illustrations of a filter output response for an illustrated input of an FIR filter corresponding to a high pass filter constructed using the low pass filter of FIG. 4A.
Figure 5B:
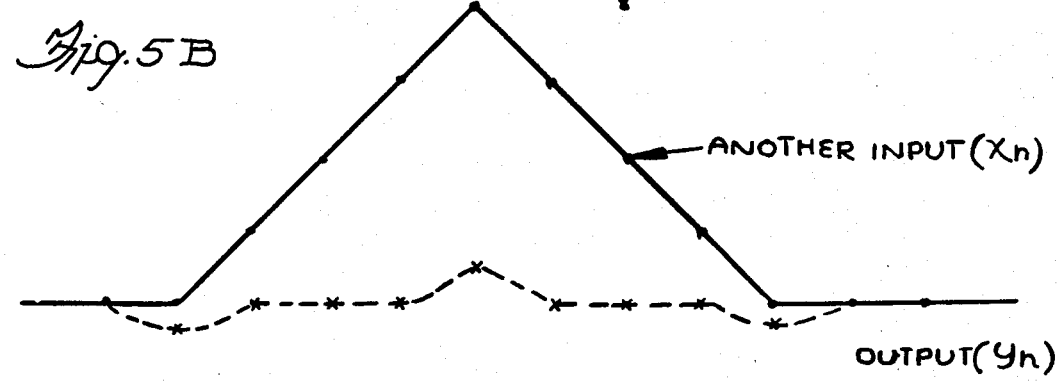

Referring to FIGS. 5A-B, a graph illustrating the filter output $(Y_n)$, corresponding to utilization of the model from FIG. 4A, is shown for two input waveforms $(X_n)$, where the filter output $Y_n = X_n - 0.5X_n - 0.25(X_{n-1}+X_{n+1}) = 0.5X_n - 0.25(X_{n-1}+X_{n+1})$.

It is clearly seen from FIGS. 5A-B that this filter exhibits almost no ringing. (For the problems encountered in using recursive sharp cutoff high pass filters see "Use of Signals in the Terminal QRS Complex to Identify Patients with Ventricular Tachycardia After Myocardial Infarction," by Dr. Michael Simson, in *Circulation*, Vol. 64, No. 2, and especially see FIG. 1 on page 237.)

Figure 6:
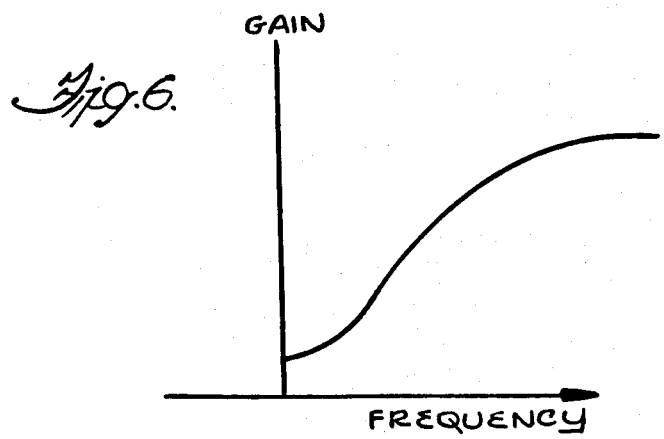
FIG. 6 is a graphical illustration of an FIR high pass filter frequency response corresponding to a high pass filter constructed using the low pass filter of FIG. 4C.

Referring to FIG. 6, the frequency response of Gaussian high pass filter is shown, corresponding to the Gaussian low pass filter according to the relationship:

Gaussion High Pass Output = 1 − (Gaussian Low Pass Output). The Gaussian high pass frequency response curve can be shaped by controlling the width of the Gaussian low pass curve. In practice, the filter response must be truncated to finite terms. An FIR approximation for the Gaussian high pass filter can be readily constructed in a straightforward manner.

Figure 7:
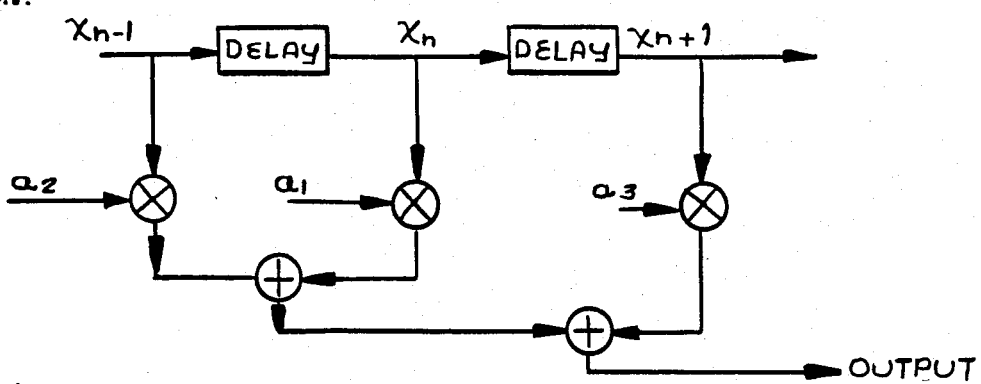
FIG. 7 is a system block diagram of one realization of an FIR filter of the type illustrated in FIGS. 5A, 5B.
Figure 8:
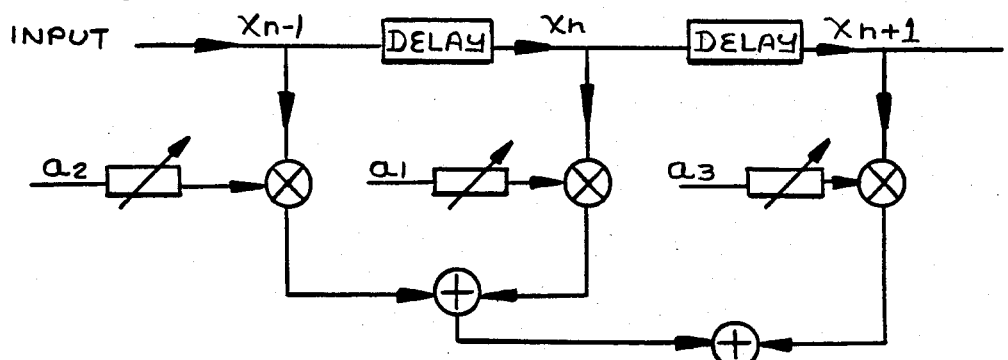
FIG. 8 is a system block diagram of a realization of an adaptive FIR filter of the type illustrated in FIG. 7.

The realization of the FIR filters is generally represented as $Y_n = A_1 * X_n + A_2 * X_{n-1} + A_3 * X_{n+1} + \ldots$ An implementation of a high pass filter of the type modeled in FIGS. 5A, 5B is illustrated in FIG. 7, for $Y_n = A_1 X_n + A_2 X_{n-1} + A_3 X_{n+1}$ where $A_1 = 0.5$, $A_2 = -0.25$, and $A_3 = -0.25$ This filter can be constructed in a straightforward manner in hardware or software. FIR filters can also be used adaptively for time-varying filtering, where the coefficients can be changed as a function of the input and/or output signal, or as a function of time. Thus, the filter response can change to attain optimum response for a given input function. For example, where the filter is output is of high amplitude and is not changing in a wavy manner, the filter response can be adapted to have a sharper high pass cutoff, thus making detection more reliable. An illustration of an adaptive FIR high pass filter is shown in FIG. 8.

FIR filters can additionally be implemented simply as a weighted average. Thus if $\{I_n\}$ is an input sequence and $\{Q_n\}$ is the output sequence, then $$Q_n = \sum_{m=-l}^{m=+l} a_m I_{n-m}$$

where $a_m$ are preselected coefficients. Thus, the filter uses "l" samples on both sides of the sample "n" to obtain the filtered output. The filter spread is said to be $(2l+1)$, since $(2l+1)$ input samples are used to derive an output. Choise of coefficients determines the characteristics of the filter. Several methods of design of these coefficients exist. Digital filters are well-known in the art, and will not be discussed in general terms in any substantial detail herein. Reference is made, however, to two recognized works [i.e., *Digital Signal Analysis* by S. D. Stearns, Hayden Book Company, Inc., (1975) pp. 182-222; and *Digital Signal Processing* by Oppenheim and Schafer, Prentice-Hall, Inc., (1975) pp. 195-282], the contents of both of which are incorporated herein by reference. The aforementioned excerpts teach, in detail, the methods for designing various digital implementations of analog filters. Another reference book teaching similar methods is *Theory and Application of Digital Processing* by Rabner and Gold, Prentice-Hall, Inc.

Figure 9:
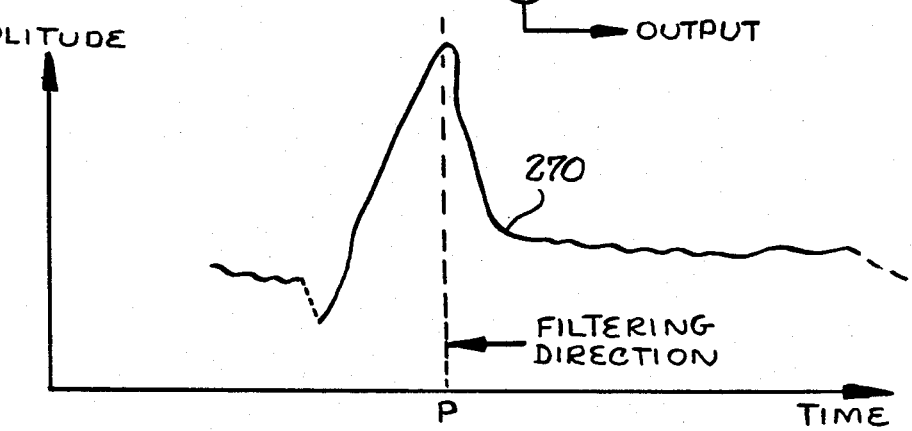
FIGS. 9-11 are graphical illustrations of a filtering technique utilizing finite impulse response filters in accordance with one embodiment of the present invention.
Figure 10:
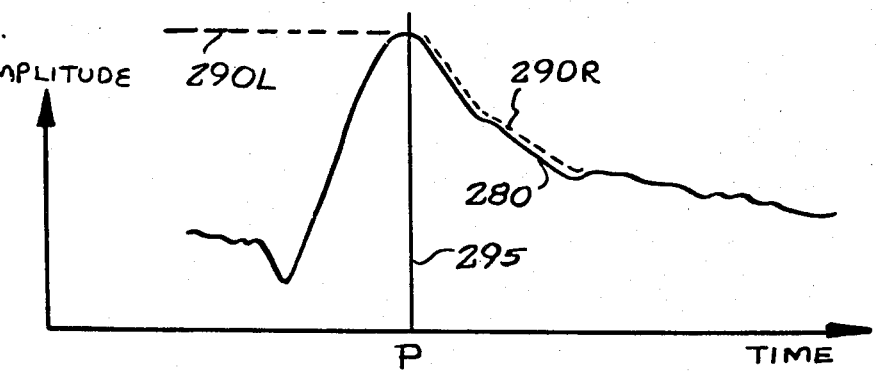
Figure 11:
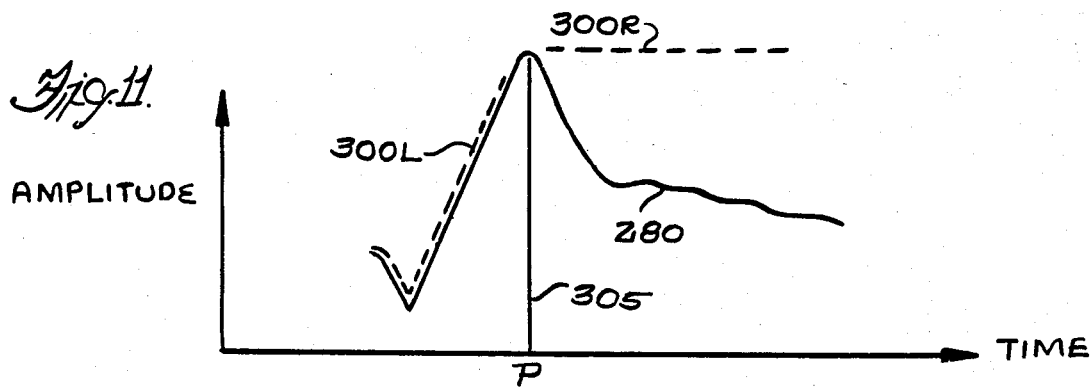

It is straightforward to design a certain set of coefficients which yields the desired proper characteristics, i.e. adaptive high pass filter characteristics. In order to avoid "spill-over" (e.g. ringing effects) in the tail of the QRS portion of the ECG input from affecting adjacent samples (which in turn affect the filter output), adpative filtering in accordance with the teachings of the present invention can be used, as illustrated in FIGS. 9-11. Either forward only or reverse only (backwards in time) filtering direction can be used. If so desired, a combination of forward and reverse direction filtering can be used.

Assuming for sake of illustration that the reverse only filtering direction is selected, waveform analysis would commence at the right side of the waveform, sample number $n=512$ (end of waveform), where n=a running index of the current sample number. (forward filtering would commence with $n=1$).

The peak "p" of each ECG input waveform is determined for each ECG cycle as described above herein. The filtering can then proceed as described below.

Referring to FIG. 9, a sample waveform 270 to be filtered is shown. The filter output can be defined as $$Q_n = \sum_{m=-l}^{m=+l} a_m *$$

$I_{n+m}$, where the filter input sample spread is defined as $2l+1$.

(For either direction of filtering, $I_{n+m}$ can be replaced by $I_{n-m}$.) For filtering of $n>p+l$, i.e. $n=p+l+1, \ldots 512$, then $I_{n+m}=0$ for $n+m=512$. For filtering of $p+l>n>p$, a portion of the input samples used by the filter in deriving an output occur on the $n<p$ side of the input waveform, which should not be allowed to change the filter output for $p+l>n>p$.

To prevent the samples $n<p$ from affecting the filter output for $p+l>n>p$, the waveform is effectively extended by a constant for $n<p$ such that $I_{n+m}=I_p$ for all $n+m<p$, as shown by the dotted line 290L in FIG. 10. The resultant waveform 290R produces a filter output whenever $n \geq p$ but $n<p+l$.

This has the effect of eliminating "spill-over" from the left-hand side ($n<p$) to the right-hand side ($n>p$) of the input waveform. Since the filter is high pass, the extension of the waveform by a constant has no effect on the filter output. In a similar manner, for filtering of $n<p$, the waveform 280 is extended by a constant as shown by dashed line 300R on the right-hand side of the peak p, such that $I_{n+m}=I_p$ for $n>p$, as shown in FIG. 11. This has the effect of eliminating spill-over from the right-hand side ($n>p$) to the left-hand side ($n<p$) of the input waveform illustrated by dashed line 300L. The net effect is that ringing artifacts are reduced to almost zero, while complete filtering action is preserved. The reference characteristic need not be limited to the peak p, and can be chosen according to desired filtering characteristics and known waveform criteria. Additionally, other adaptive and finite implulse response high pass filters can be constructed in accordance with the teachings of the present invention.

Figure 12:
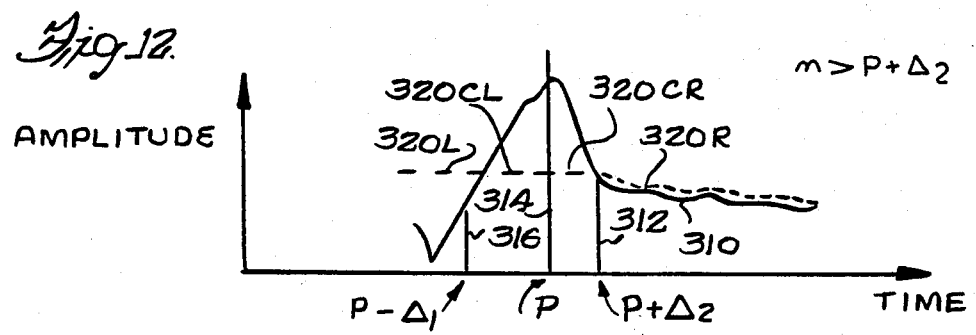
FIGS. 12-14 are graphical illustrations of a filtering technique utilizing finite impulse response filters in accordance with another embodiment of the present invention.
Figure 13:
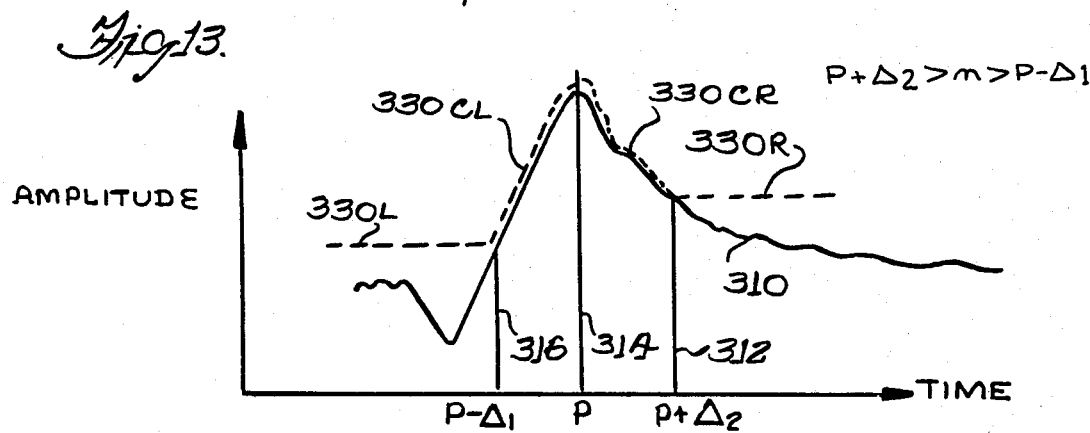
Figure 14:
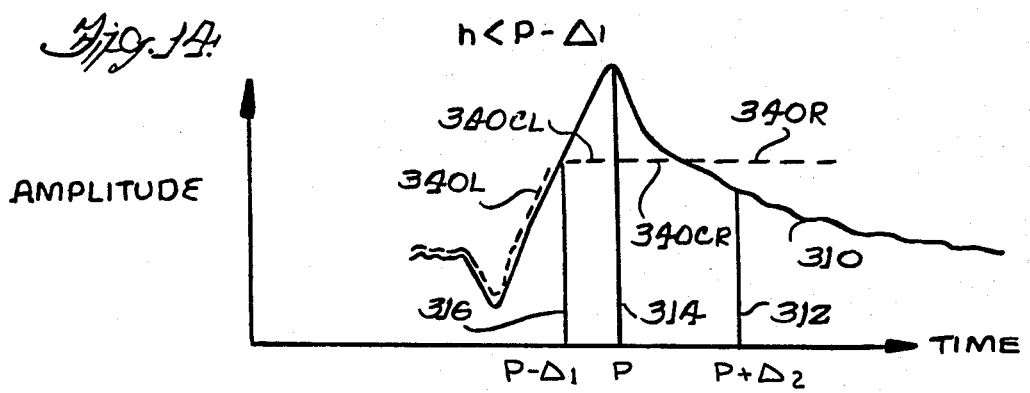

Referring to FIGS. 12-14, a preferred alternative high pass filtering embodiment of the present invention are illustrated where two reference sample position numbers, $\Delta 1$ and $\Delta 2$, are chosen as waveform extension breakpoints, in addition to determination of the peak position reference number p. The filter output is designated $Q_n$, where $$Q_n = \sum_{m=-l}^{m=+l} a_m I_{n+m}.$$

Referring to FIG. 12, filtering for $n>p+\Delta 2$ is shown as dashed line 320R, where the sampled input waveform 310 is extended by a constant along dashed lines 320CR, 320CL, 320L such that $I_{n+m}=I_{p+\Delta 2}$ for $n+m<p+\Delta 2$.

Referring to FIG. 13, filtering for $p-\Delta 1<n<p+\Delta 2$ is shown, where the sampled input waveform 310 is extended by a constant, along dashed lines 330L, 330R such that $I_{n+m}=I_{p+\Delta 2}$ for $n+m>p+\Delta 2$ and $I_{n+m}=I_{p-\Delta 1}$ for $n+m<p-\Delta 1$.

Referring to FIG. 14, filtering for $n<p-\Delta 1$ is shown, where the sampled input waveform 310 is extended by a constant along dashed line 340R such that $I_{n+m}=I_{p-\Delta 1}$ for $n+m>p-\Delta 1$.

Since the filtered values inside the QRS complex portion of the ECG input are not of much interest in the prediction of the ventricular tachycardia, the above described filtering technique will work extremely well. The values for $\Delta 1$ and $\Delta 2$ should be experimentally determined to insure best results.

Many other alternatives exist other than those illustrated in FIGS. 12-14. For example, if filtering is desired for $p+\Delta 2>n>p$, then the sampled input waveform is extended by a constant, twice, such that $I_{n+m}=I_{p+\Delta 2}$, for $n+m>p+\Delta 2$, and $I_{n+m}=I_p$ for $n+m<p$. Again, experimentation can determine which technique will work best for the particular test equipment utilized and the particular data characteristics which are to be analyzed.

Returning again to FIG. 1, the filter 170 provides a filter output 175 in accordance with the teachings of the present invention. The filter output 175 is coupled to means 200 for processing the filter output to determine the amount of high frequency energy in the late portion of QRS complex (QRS tail).

The portion of the filtered QRS which corresponds to the late section containing the potential high frequency energy of interest must be located. This can be achieved by first selecting a 40 millisecond sample substantially after the termination of the major portion of the QRS (e.g., t=300 ms to t=260 ms) and averaging the $V_n$ values to achieve an average noise voltage for that sample. That average noise is stored, and a standared noise level deviation is calculated employing the following equation:

$$\text{Standard deviation} = \sqrt{\frac{\sum_{n=260}^{n=300} V_n^2 - \left(\frac{\sum_{n=260}^{n=300} V_n}{40}\right)^2}{39}}$$

This standard noise deviation is stored, and a 5 millisecond sample of the QRS is selected (e.g., from t=250 ms to t=255 ms). The average value of the time segment voltages from t=250 ms to t=255 ms is calculated and compared to the average noise level plus three standard deviations (as previously determined). If the calculated value for the 5 millisecond sample does not exceed the total, the time segment is decremented by one time slot (i.e., one millisecond), and the process repeated until the selected average voltage of the smaple does exceed the level of the calculated noise plus three standard deviations. This occurrence indicates that the selection process has arrived at the termination of the QRS signal (i.e., the middle time segment of the 5 millisecond sample is defined as the end of the QRS.)

In order to determine whether the QRS signal has or does not have the high frequency tail referred to above, the voltage sample in the middle time segment ($t_s$) of the 5 millisecond sample is then selected as well as the next lower 39 voltage time segments (e.g., from t=255 to t=186). The foot mean square value of all of these voltages is then calculated as:

$$V_{RMS} = \sqrt{\frac{V_n^2(t_s) + V_n^2(t_s-n) + \ldots V_n^2(t_s-40)}{40}}$$

The RMS voltage of the 40 ms sample is then compared to 25 microvolts, and if it exceeds 25 microvolts it is indicative that the patient is not susceptible to ventricular tachycardia whereas, if it is less than 25 microvolts it is indicative that the patient is subject to ventricular tachycardia. Medical researchers have found that the high frequency component found in patients with ventricular tachycardia extends the tail of the QRS by several tens of milliseconds, but at a relatively low level. Thus, a low level measurement indicates that there is a low level, high frequency tail of energy appended to the QRS. If the voltage exceeds the 25 microvolt level, it is indicative that, in lieu of there being the aforementioned tail of high frequency energy, the measurement is actually being made on the major portion of the QRS signal which has high levels of high frequency energy. The results of these tests can be displayed or printed out as shown in FIG. 1 for the physician's use. Parameters such as 40 milliseconds, 5 milliseconds, and 25 microvolts should be optimized for the selected filter characteristics. Also, squares used in the $V_{RMS}$ and standard deviation equations can be replaced by absolute values.

The filter output 175 is also coupled to means 210 for determining the duration of the QRS portion of the ECG waveform. The width of the QRS waveform has been found to have a relationship to a patient with ventricular tachycardia. In order to measure the width of the QRS in the above system, it is sufficient to obtain an indication of the beginning of the QRS waveform, as the end of the QRS has already been determined. The initiation of the QRS is calculated in much the same manner. In specific, from t=40 to t=1, a 40-millisecond sample of noise measurements is averaged, and the standard deviation calculated. Five (5) millisecond values are then selected and tested to determine whether the average value of each 5-millisecond sample exceeds the average noise plus three standard deviations. For the 5-millisecond sample which does exceed that level, the beginning of the QRS is then defined as the middle time segment of that 5-millisecond segment. The duration of the QRS then stretches from the middle of that segment to the end of the QRS as defined above. Again squares can be replaced by absolute values.

Referring to FIGS. 15A-D, a flow chart of the overall processing flow utilized to predict ventricular tachycardia from an ECG input in accordance with the illustrated embodiments of the present invention is shown. The starting point of the flow chart is based on the assumption that an electrocardiograph has been attached to a subject patient. The X, Y, and Z ECG leads waveforms are periodically sampled during each of a plurality of ECG waveform input cycles, each ECG cycle corresponding to a heart beat, as shown in box 500. Separate sampling is done for each of the X, Y, and Z input leads. The samples are filtered to reduce noise artifacts, as shown in box 502, and the filtered samples are digitized as shown in box 504. The digitized samples are stored in a secondary storage, as shown in box 506. A beat count is initialized at 0, as shown in box 508, which tracks the number of beats utilized in subsequent steps in averaging and determining waveform features. The digitized X lead QRS waveforms are accessed from the secondary storage, and the beat count is incremented, box 512. Selected features of the accessed waveform are computed, box 520, and the values of the reference sample points for the selected features are stored, box 530. The beat count value is tested, as illustrated for a count of 4, at box 540, to track the number of input waveforms utilized in obtaining the averaged values. If the beat count is not yet 4, or whatever other number may be determined as desirable, the process returns to step 510 and continues to access waveform samples. If the waveform beat count is equal to 4, then the process continues at box 550, where the values of the features for the 4 beats are averaged to determine reference features.

Next, another QRS X lead input is accessed from secondary storage, and the selected features are computed for it, box 560. If the computed features as determined at box 560 are sufficiently close to the reference features as determined at box 550, then the waveform accessed at box 560 is utilized as an acceptable input. If the features of the sampled waveform as determined at box 560 differ significantly from the reference featues as determined at box 550, then the signal waveform accessed at box 560 is rejected as an invalid signal, and processing returns to box 560 for accessing of another QRS X lead input. Where the sampled waveform of box 560 is found acceptable by decision logic as shown at box 570, processing proceeds at box 580. The QRS voltage values of all accepted QRS waveforms for the X lead are averaged, box 580, and the averaged values are stored, box 590. The steps from 560 to 590 are repeated for one hundred and fifty (150), or whatever other number is determined desirable, QRS X lead waveform inputs as shown at box 600. Next, the steps from 508 to 600 are repeated, for the Y, and then Z, QRS lead waveform inputs. Thus, as the system completes the process to the step of box 610, averaged X, Y, and Z waveform samples are provided for a single averaged ECG cycle. For reference sake, the averaged samples are designated $X_n$, $Y_n$, and $Z_n$, corresponding to the averaged X, Y, and Z, waveforms, respectively, where n equals the reference sample point within the given ECG cycle, such as n=1 to 512, as shown at box 620.

Next, the peak value of the averaged waveform samples is determined, first for the X averaged waveform, as shown at box 630, and then for the Y and Z averaged samples, as shown at box 640. Then, the average value of n, designated $n_p$, at which the peak of the $X_n$, $Y_n$, and $Z_n$ averaged waveforms occurs is determined, as shown at box 650. As described herein with reference to FIGS. 12-14, $\Delta 1$ and $\Delta 2$, are selected, as shown at box 660. Next, the filter output, $Q_n$, is obtained from each of the averaged input samples $X_n$, $Y_n$, and $Z_n$ respectively, and separately, as shown at boxes 670 to 750.

The filter output is obtained by adaptively filtering the averaged input waveform samples in a sectional manner. The sectioning is done based on the reference sample position, n, where the input $\{X_n\}$ is modified to eliminate ringing effects outside the section being analyzed. This technique is described herein with reference to FIGS. 9-14. For example, as illustrated at box 670, to obtain a filter output for the section of the input sample waveform of $n \geq p + \Delta 2$ a new input X' is created, where $X_n' = X_n$, the original input waveform average sample values, for $n > n_p + \Delta 2$, thereby maintaining the integrity of the filtering action for those sample values, while creating in an adaptive manner a new input $X'_n = X_{n_p + \Delta 2}$ for all values of $n < n_p + \Delta 2$.

The next step is to initialize the value of n for the filtering action. Where forward filtering is used n+0 is the initialized value. Where backwards filtering is used (reverse time filtering), n is initialized at n+512, as shown at box 680. A filter output $Q_n(X)$ is obtained for the section $n \geq n_p + \Delta 2$, as shown by box 690. The filtering action is implemented by decrementing n for backward filtering or by incrementing n for forward filtering. The filter output $Q_n(X)$ is the summation of the filter output for the combination of input samples utilized in obtaining the output. The next step is to obtain a filter output for a different section of the averaged input waveform. For obtaining a filter output for $n_p - \Delta 1 \leq n < n_p + \Delta 2$, as shown at box 700, a new input is created $X_n'' = X_n$ for $n \leq n_p + \Delta 2$, and $X_n'' = X_{p + \Delta 2}$ for $n > n_p + \Delta 2$. Finally, a filter output is obtained for the section of the averaged sample input waveform for $n < n_p - \Delta 1$, as shown in box 720. This is done by creating a new input X''' which is adaptive to the section of the averaged input waveform being sampled by the filter, such that $X''' = X_n$ for $n \leq n_p - \Delta 1$, and $X''' = X_{np - \Delta L}$ for $n > np - \Delta 1$. The net filter output for the three sections of the averaged X lead sample inputs is equal to the sum of the filter outputs as derived at boxes 690, 710, and 730. The filtering steps 670 to 730 are repeated for the Y lead averaged sample inputs and then for the Z lead averaged sample inputs to derive outputs $Q_n(Y)$ and $Q_n(Z)$, as shown ab box 740.

A composite filter output is then computed as $V_n = |Q_n(X)| + |Q_n(Y)| + |Q_n(Z)|$, and the composite filter is output designated $V_n$, as shown in box 750. An average noise voltage value $\overline{V}_n$ is calculated as $$\overline{V}_n = \frac{1}{40} \sum_{n=260}^{n=300} V_n,$$

and resultant value $\overline{V}_n$ is stored, as shown at box 760. The use of samples 260 to 300 is based upon experimental data published in medical periodicals indicating that samples 260 to 300 represent the tail of the QRS waveform. The use of these samples numbers, and of the 40 sample total, in computing the average noise voltage can be changed as determined by experimental results. Next, a composite standard deviation is computed, equal to $$CSD = \left[ \sum_{n=260}^{n=300} (V_n - V_n)/40 \right]^{\frac{1}{2}}.$$

The resulting composite standard deviation is then stored, as shown at box 770. Where samples 260 to 300 are utilized for boxes 760 and 770, a 5 millisecond segment of $V_n$ is averaged and called $\overline{\overline{V}}_n$, with n starting at n=300, with n decreasing for reverse filtering. The value $\overline{\overline{V}}_n$ as determined at box 780 is compared to a reference level Vref=$\overline{V}_n$+3$\times$CSD, as shown at box 790, and if the average value $\overline{\overline{V}}_n$ is less than V ref, then the value of n is decremented, and a new 5 millisecond segment is selected. Where the value of the averaged 5 millisecond segment is greater than V ref, processing proceeds at box 810, and a voltage sample is selected in the middle of the 5 millisecond segment, plus in the middle of the next 39 time segment samples. The RMS voltage $V_{rms}$ is computed for these 40 samples as $$V_{rms} = \sum_{n=1}^{n=40} V_n^2 (t_{s-n})/40,$$

as shown at box 820. The RMS voltage $V_{rms}$ is compared to a reference level as determined by experimentation, such as 25 microvolts, as shown at box 830, said reference level being a threshold indicative of ventricular tachycardia. Where the RMS voltage is greater than the reference level, indicating the absence of potential ventricular tachycardia, an appropriate indication is given as shown at box 870. Where the RMS voltage is less than the reference level, then processing proceeds from box 830 to box 860 where indication of potential ventricular tachycardia is given.

In parallel to steps 760 to 830, the duration of the QRS complex of the filtered ECG input waveform is derived from the filter output, as shown at box 840. The QRS duration is then compared to a threshold value T, as shown in box 850, which reference value is a threshold for detecting potential ventricular tachycardia. When the QRS duration is determined to be less than the threshold, ventricular tachycardia is indicated, and proper indication is provided to the user of the system as shown at box 860. Where the QRS duration is greater than the threshold T, an indication of no potential ventricular tachycardia is provided as shown at box 870. Where there is a positive indication of potential ventricular tachycardia provided by the RMS voltage decision box 830, and a negative indication of potential ventricular tachycardia from the QRS duration decision box 850, or vice versa, an indication is provided to the user of the conflicting measurements, and the measurement steps are repeated again, starting at step 500, as shown at box 880.

The flow chart and description of FIGS. 15A-15D are meant to be illustrative only, and should not be construed in a limiting sense. Many other processing flows could be utilized, and, as described elsewhere within this specification, alternative techniques of determining high frequency low amplitude energy from the noise content of the sampled waveform exist (such as utilizing a method different from the 5 millisecond sample stepping window technique). Other alternative means of indicating potential ventricular tachycardia and conflicting QRS duration and Vrms data can be provided. Additionally, other reference parameters can be utilized in addition to or in place of QRS duration and Vrms voltage of the high frequency contents in the tail of the QRS complex portion.

Heretofore, the use of recursive sharp cutoff filters has been ineffective in unidirectional filtering of the late QRS portion of the ECG to predict VT, due to ringing and masking problems.

In accordance with one aspect of the present invention, the filter output of either a high pass, recursive, sharp cutoff IIR filter or an FIR high pass filter or an adaptive high pass filter is analyzed by taking the time derivative of the late QRS portion of the ECG, for example with means 203 in FIG. 1 in either a forward only or reverse only direction, or bidirectionally. A resultant derivative waveform "reference" pattern is then established for two control groups (1) non-VT and (2) VT. In one embodiment the first time derivative is used. Alternative embodiments utilize second and higher order time derivatives. Additionally, other linear and differential techniques can be used to transform the signal and retain the information for analysis. Furthermore, other pattern recognition techniques can be utilized in analyzing the signal. Additionally, where two or more linear processes are utilized, the result of processing is the same regardless of the order. Thus, filtering and differentiating can occur in either order. Each control group will exhibit a unique reference pattern easily distinguishable from each other.

Even the ringing artifacts of the sharp cutoff recursive IIR filters result in derivative waveforms which have distinguishable VT and non-VT reference patterns. Derivative analysis is best implemented where the signal waveform being differentiated exhibits a high signal to noise (S/N ratio).

It is well known in the art that noise can add extraneous components to a signal waveform, which can cause problems. It is therefore desirable to maximize the S/N ratio. All of the waveforms illustrated herein are clean with good S/N ratios.

Analysis of the derivative waveforms can be done by numerous techniques, such as evaluating the number of positive and negative transitions, evaluating the area of positive and negative pulses about a reference line, etc.

The present invention can be practiced in analog or digital form. However, digital filtering provides cleaner filter output and allows the use of signal averaging, templating, and other techniques. Finite and/or infinite pulse response filters and/or adaptive filters can be utilized with the present invention.

Referring now to FIGS. 16 and 17, certain waveforms are shown representing the output of the high pass filter for the late portion of the QRS complex in a control group without ventricular tachycardia waveforms A, B, C of FIG. 16 and patients with ventricular tachycardia representing the second control group waveforms A, B, C of FIG. 17. These outputs are obtained by constructing a digital filter having a Butterworth high pass filter response, and utilizing signal averaging prior to filtering in a reverse direction. The waveforms of FIGS. 16 and 17 represent clinically derived data which was published in a medical periodical, Circulation, Volume 64, No. 2, August 1981, pages 235-242, entitled "Use Of Signals In The Terminal QRS Complex To Identify Patients With Ventricular Tachycardia After Myocardial Infarction", by Dr. Michael Simson, M.D., and specifically page 238, FIG. 3. These curves were obtained by signal processing in patients with anterior myocardia infarctions. FIGS. 18 and 19 similarly represent digital filter outputs derived from empirical data as published in the Circulation publication cited above, at page 238, FIG. 4, representing signal processing in patients with inferior myocardia infarctions. Waveform A of FIG. 18 represents a control group of patients without ventricular tachycardia, while waveform A of FIG. 19 represents the second control group with ventricular tachycardia.

Referring now to waveform B of FIGS. 16, 17, 18 and 19, the first time derivative of the respective waveform A of FIGS. 16, 17, 18 and 19, are shown. Comparing the waveform B of FIGS. 16 and 17, it is seen that the first time derivative waveforms of patients without, and with, ventricular tachycardia are substantially different in terms of the number of transitions, the duration of pulse widths, and the relative position of transitions. Additionally, the area under the pulses differs for the two curves. Thus, the prediction of ventricular tachycardia can be made in a straightforward manner from the derivative waveform curve either by human analysis or by electronic hardware analysis or by digital analysis via computer. Referring to waveform B of FIGS. 18 and 19, it is again seen that the first time derivative of the filtered ECG QRS complex waveforms provide readily distinguishable waveform patterns making detection of people with ventricular tachycardia waveform B of FIG. 19 from those without ventricular tachycardia (waveform B of FIG. 18) a relatively straightforward task. Again the number of transitions, the time position of the transitions, the pulse widths between transitions, and the areas displaced by the pulses are readily distinguishable between the resultant derivative waveforms of FIGS. 18B and 19B.

Referring to waveform C of FIGS. 16, 17, 18 and 19 the second time derivative waveforms of the filtered outputs of FIGS. 16, 17, 18 and 19 respectively, are shown. Referring to waveform C of FIGS. 16 and 17, it is seen that the non-VT versus the VT second time derivative waveforms differ significantly, and provide an easily distinguishable mechanism by which ventricular tachycardia can be predicted. The amplitude, time position, and number of transitions differs between the two waveforms C of FIGS. 16 and 17, and can be easily analyzed by a human, electronic hardware, or a digital computer system. Referring to waveform C of FIGS. 18 and 19, it is again clearly seen that the second time derivative of the filtered waveforms yields readily distinguishable characteristics for analyzing non-VT (waveform C FIG. 18) versus VT (waveform C FIG. 19) patients. The waveforms are readily distinguishable based upon the number of transitions, the amplitude of the transitions, and the time position of the transitions.

It can now be understood that utilizing the first, second, or higher time derivative of the filtered waveform yields an output by which patients with and without a propensity for ventricular tachycardia can be distinguished and analyzed.

Figure 21:
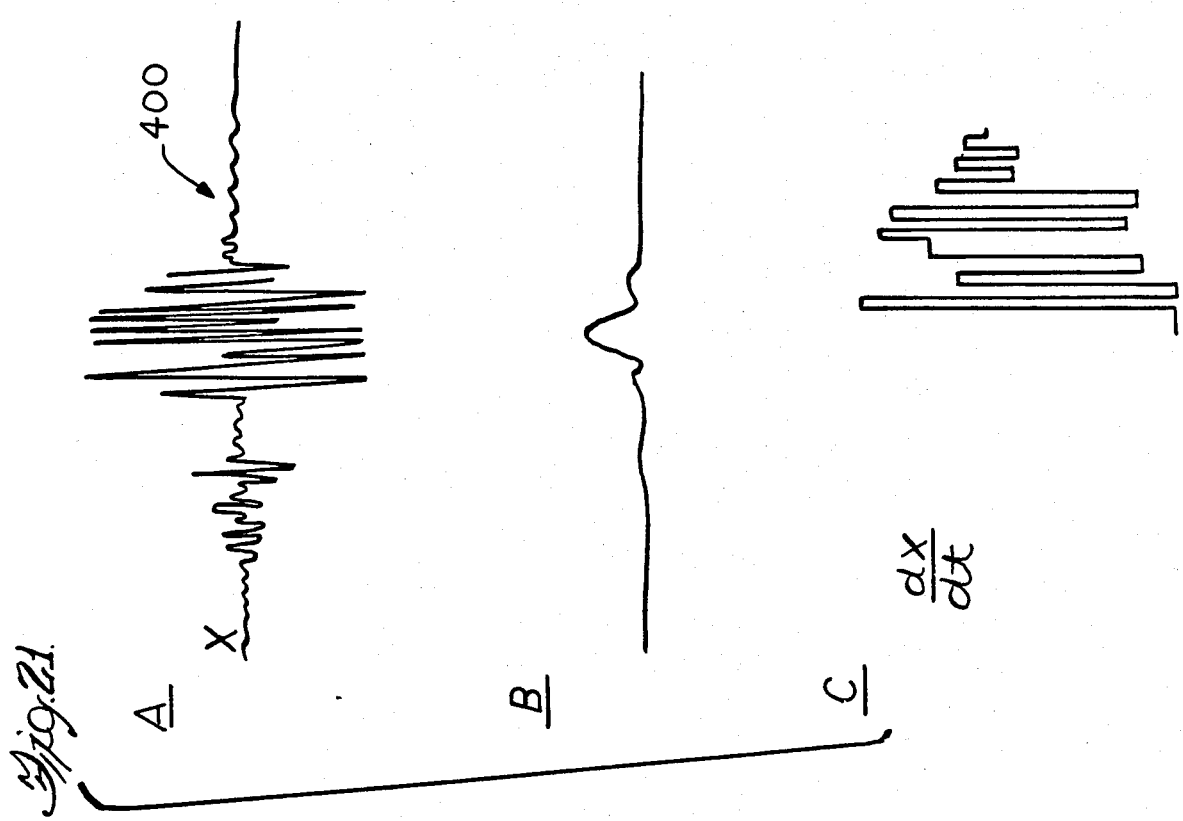
Figure 20:
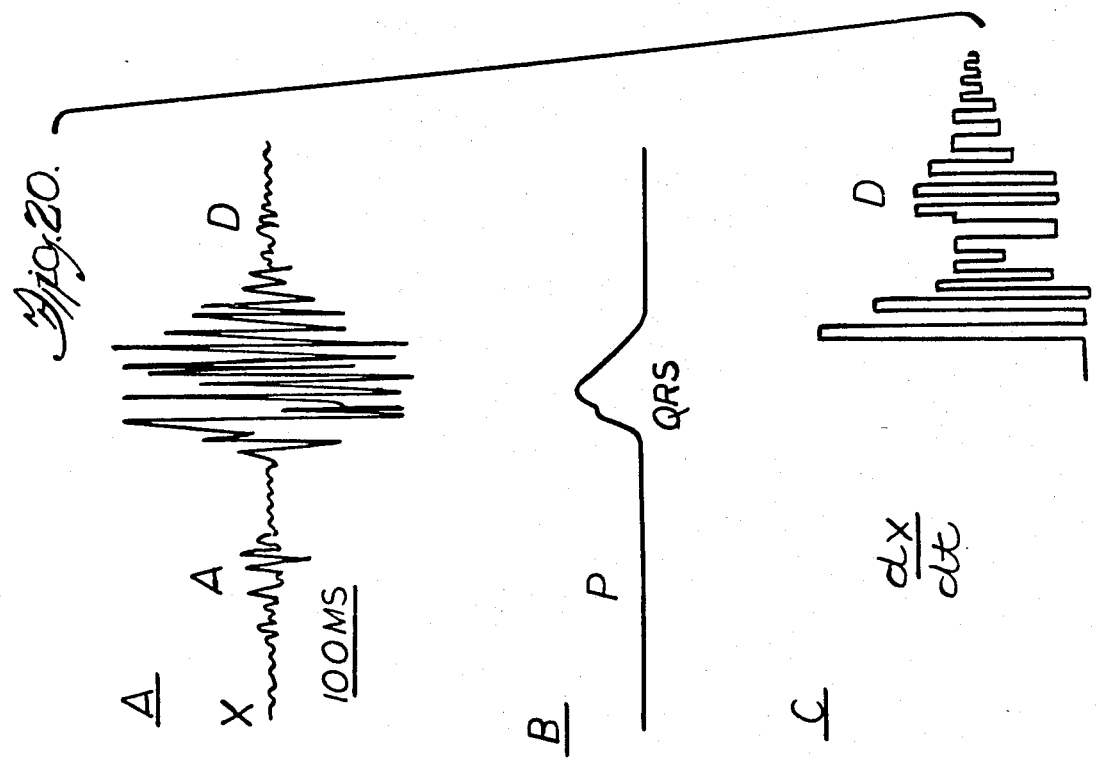

Referring to FIGS. 20 and 21, the filter outputs of electrocardiogram signals as output from recursive sharp cutoff IIR high pass filters is shown. Waveform A of FIGS. 20 and 21 show a high resolution filter output while FIGS. 20B amd 21B show the low resolution filter outputs. Waveforms A, B of FIG. 20 represent waveforms obtained from clinical tests on patients having known episodes of chronic ventricular tachycardia, while waveforms A, B of FIG. 21 represent waveforms obtained from clinical data of patients with no known episodes of chronic ventricular tachycardia but who had chronic ventricular arhythmia. The portion of the waveform marked "D" in waveform A of FIG. 20 represents the delayed waveform present in patients having known episodes of ventricular tachycardia. This data and these curves were published in the medical publication Circulation, Volume 63, No. 5, May 1981, pages 1172-1178, at page 1175, entitled "Body Surface Detection Of Delayed Depolarizations In Patients With Recurrent Ventricular Tachycardia And Left Ventricular Aneurysm", by John J. Rozanski, M.D., et al. Waveforms C in FIGS. 20 and 21 represent the first time derivative of the respective waveforms A for the relevant portion of the waveform in the time vicinity of the delayed waveform D. However, as seen by the arrow 400 in waveform A of FIG. 21, there is no delayed portion "D" occurring.

Referring now to waveforms C in FIGS. 20 and 21, the first time derivative DX/DT of the waveforms A of FIGS. 20 and 21, respectively, are shown. It is clearly seen that the first time derivative waveforms C are distinguishable from one another, each having a unique reference pattern. The number of transitions, time position of transitions, and area displaced by the pulse width between transitions differs for each of the waveforms C of FIGS. 20 and 21. Thus, it is straightforward, in the manner as discussed above, to differentiate between patients exhibiting a propensity for ventricular tachycardia versus patients not indicating a propensity for ventricular tachycardia. This can be done by human analysis, or it may be done by electronic analog or digital techniques. Additionally, second and higher order derivatives of the filtered waveform may be utilized and analyzed to distinguish the waveforms of VT and non-VT patients.

Although this invention has been described with reference to the illustrated embodiments, this description is not meant to be constructed in a limiting sense. Various modifications of the disclosed embodiments, as well as other embodiments of the invention, will become apparent to those skilled in the art upon reference to the drawings and description of the invention. It is therefore contemplated that the appended claims will cover any such modifications as fall within the true scope of the invention.

What is claimed is:

1. A system for predicting ventricular tachycardia from electrocardiograph input waveforms comprising:
   filter means for providing a high pass filter output responsive to said input waveforms,
   means for providing a time derivative output of said filter output responsive to the filter output,
   means for predicting ventricular tachycardia responsive to said time derivative output.

2. The system as in claim 1 further comprising: means for digitizing said input waveforms prior to processing by said filter means.

3. The system as in claim 2 further comprising: means for signal averaging the digitized input waveforms prior to processing by said filter means.

4. The system as in claim 1 wherein said filter means is a finite impulse response filter.

5. The system as in claim 1 further characterized in that said filter means is an adaptive high pass filter.

6. A system for predicting ventricular tachycardia from electrocardiograph input waveforms comprising:
   filter means for providing a filter output responsive to said input waveforms,
   means for providing a time derivative output of said filter output responsive to the filter output,
   means for predicting ventricular tachycardia responsive to said time derivative output.

7. A ventricular tachycardia prediction system for use with an ECG input having cyclical characteristics comprising:
   means for periodically sampling the ECG input during each of a plurality of ECG cycles,
   filter means for unidirectionally filtering the signals for each ECG cycle, so as to provide a filter output systematically related to the high frequency content of the ECG input;
   means for providing a reference signal;
   means for comparing the filter output to the reference signal; and
   means for indicating a propensity for episodes of ventricular tachycardia responsive to said means for comparing.

8. The system as in claim 7 wherin said samples are filtered in the same time order as the ECG input was sampled.

9. The system as in claim 7 wherein said samples are filtered in the reverse time order as that which the ECG input was sampled.

10. The system as in claim 8 or 9 wherein said filter means is further comprised of:
    means for averaging samples for a plurality of ECG cycles prior to deriving the filter output.

11. The system as in claim 7 further comprising:
    means for determining the duration of the QRS portion of the ECG signal responsive to said filter output;
    second means for comparing said determined duration to said second reference signal, and
    means for indicating the prediction of ventricular tachycardia responsive to said second means for comparing.

12. The system as in claim 7 wherein said reference signal corresponds to a filter output indicative of a high frequency, low level, energy component in the tail of the ECG waveform.

13. A method for predicting ventricular tachycardia in a patient from cyclically recurring ECG inputs, comprising the steps of:
    sampling and storing a plurality of points each ECG cycle at a fixed rate of N samples per cycle;
    identifying a reference point p of the waveform,
    deriving a filter output $Q_n$ responsive to unidirectionally filtering the stored samples,
    providing a preselected reference signal, comparing the filter output to said reference signal and indicating the prediction of potential ventricular tachycardia responsive to said comparison.

14. A method for analyzing electrocardiograph signals to determine the presence or absence of a predetermined level of high frequency energy in the late QRS signal, comprising the steps of:

sampling a series of analog QRS signals at spaced time segments, converting each segment sample to a digital signal equivalent, applying a portion of said digital signals in a single time direction to a filter;

determining an arithmetic value of the amplitude of the output of said filter; and comparing said value with said predetermined level.

15. The method of claim 14 further characterized in that said filter has a high pass response.

16. The method of claim 14 further comprising the step of generating an indication signal which is a function of said comparison.

17. The method of claim 14 further including the step of averaging the digital values of said series of QRS signals to obtain an averaged composite QRS signal before the application thereof to said filter.

18. The method of claim 17 wherein said portion of said digital signals comprises signals representing at least the last 40 milliseconds of the averaged QRS signal.

19. The method of claim 16 further including the step of measuring the duration of said averaged QRS signal.

20. A system for analyzing electrocardiograph signals to determine the level of high frequency energy in the late QRS signal comprising:

means for converting X, Y, and Z lead electrocardiographic input signals to digital signals representative of times spaced samples;

means for examining said X, Y, and Z digital signals and selecting therefrom the QRS waveform portions thereof;

means for signal averaging a multiplicity of said selected QRS waveforms for each of said X, Y, and Z inputs and providing composite, digital signals representative of the averaged X, Y, and Z QRS waveforms;

filter means having a preselected response;

means for applying to said filter means in a forward time order the digital signals representative of the late portion of each of said X, Y, and Z QRS waveforms;

means for providing a reference signal; and means for comparing the output of said filter means with said reference signal to determine the presence of a high frequency, low level, energy component in the filter output predictive of ventricular tachycardia.

21. The system of claim 20 wherein said comparing means compares only a portion of said filter's output.

22. The system of claim 21 wherein said portion of said filter's output represents the filtered last 40 milliseconds of the QRS waveform.

23. The system of claim 22 wherein said comparing means combines selected portions of said filter's output for each of the X, Y, and Z signal samples and determines an arithmetic value of said combined portions.

24. The system of claim 23 wherein said arithmetic value is the root mean square of said combined portions.

25. The system as in claim 24 wherein said arithmetic value is the sum of the absolute values of the filter outputs for each of said X, Y, and Z signals.

26. The system of claim 20 further comprising:

means for applying to said filter means the digital signals representative of the early portion of each of said X, Y, and Z QRS waveforms;

means for extracting from said filter's output the time of commencement of said QRS waveforms;

means responsive to said extraction means and said comparing means for determining the width of said QRS waveform;

means for providing a width reference signal, means for indicating the prediction of probable ventricular tachycardia responsive to a comparison of the determined QRS width and the width reference signal.

* * * * *

UNITED STATES PATENT AND TRADEMARK OFFICE
CERTIFICATE OF CORRECTION

PATENT NO. : 4,492,235
DATED : January 8, 1985
INVENTOR(S) : David H. Sitrick

It is certified that error appears in the above-identified patent and that said Letters Patent is hereby corrected as shown below:

In the Abstract, line 10, "of" should read --or--

Column 1, line 10, "accute" should read --acute--

Column 1, line 22, after "detected" delete the comma (,)

Column 1, line 23, after "amplitude" insert a comma (,)

Column 3, line 56, "In" should not begin a new paragraph

Column 4, line 59, "diagnosis" should read --prediction--

Column 4, line 62, begin new paragraph with --A plotter--

Column 8, line 14, "stop" should read --step--

Column 9, line 9, "choise" should read --choice--

Column 9, line 30, "adpative" should read --adaptive--

Column 11, lines 23-24, "smaple" should read --sample--

Column 12, line 58, "featues" should read --features--

Column 17, line 10, "amd" should read --and--

Column 17, line 17, "arhythmia" should read --arrhythmia--

UNITED STATES PATENT AND TRADEMARK OFFICE
CERTIFICATE OF CORRECTION

PATENT NO. : 4,492,235
DATED : January 8, 1985
INVENTOR(S) : David H. Sitrick

It is certified that error appears in the above-identified patent and that said Letters Patent is hereby corrected as shown below:

Column 17, line 54, "constructed" should read

--construed--

Column 18, line 37, "wherin" should read --wherein--

Signed and Sealed this

Twenty-fourth Day of September 1985

[SEAL]

Attest:

DONALD J. QUIGG

*Attesting Officer*

*Commissioner of Patents and Trademarks—Designate*